US007052872B1

(12) United States Patent
Hansen et al.

(10) Patent No.: US 7,052,872 B1
(45) Date of Patent: May 30, 2006

(54) BI-SPECIFIC ANTIBODIES FOR PRE-TARGETING DIAGNOSIS AND THERAPY

(75) Inventors: Hans J. Hansen, Slidell, LA (US); Gary L. Griffiths, Morristown, NJ (US); Shui-on Leung, Morris Township, NJ (US); William J. McBride, Summit, NJ (US); Zhengxing Qu, Warren, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 0 days.

(21) Appl. No.: 09/382,186

(22) Filed: Aug. 23, 1999

Related U.S. Application Data

(63) Continuation-in-part of application No. 09/337,756, filed on Jun. 22, 1999.

(51) Int. Cl.
*A61K 39/395* (2006.01)
*C07K 16/00* (2006.01)
*C12P 21/04* (2006.01)

(52) U.S. Cl. ............... 435/69.6; 424/136.1; 530/387.3; 536/23.53

(58) Field of Classification Search ............ 424/136.1; 435/69.6; 530/387.3; 536/23.53
See application file for complete search history.

(56) References Cited

U.S. PATENT DOCUMENTS

| 5,274,076 | A |   | 12/1993 | Barbet et al. |          |
|-----------|---|---|---------|---------------|----------|
| 5,591,828 | A |   | 1/1997  | Bosslet et al.| 530/387.3|
| 5,959,083 | A | * | 9/1999  | Bosslet et al.| 530/387.3|
| 6,096,289 | A |   | 8/2000  | Goldenberg    |          |

FOREIGN PATENT DOCUMENTS

| EP | 0263046      |   | 4/1988  |
|----|--------------|---|---------|
| EP | 0 419 387 A1 |   | 9/1990  |
| EP | 0511011 A    |   | 10/1992 |
| EP | 0517024      | * | 12/1992 |
| EP | 0 623 675 A1 |   | 11/1993 |
| WO | WO 96/04313  |   | 2/1996  |
| WO | WO 99/66951 A2|  | 12/1999 |

OTHER PUBLICATIONS

De Jonge et al, Molecular Immunology, 32, 1405-1412, 1995.*
Van Spriel et al, Immunology Today, 21, 391-396, 2000.*
Hawkins, et al.; "Delivery of Radionuclides to Pretargeted Monoclonal, Antibodies Using Dihydrofolate Reductase and Methotrexagte in an Affinity System,"; *Cancer Research*; vol. 53; May 1993; pp. 2368-2373.
Goodwin et al.; "Pre-Targeted Immunoscintigraphy of Murine Tumors with Indium-111-Bifunctional Haptens,"; *J. Nucl, Med.*; vol. 29; 1998; pp. 226-234.

(Continued)

*Primary Examiner*—David Saunders
(74) *Attorney, Agent, or Firm*—Faegre & Benson LLP

(57) ABSTRACT

The present invention relates to a bi-specific antibody or antibody fragment having at least one arm that specifically binds a targeted tissue and at least one other arm that specifically binds a targetable conjugate. The targetable conjugate comprises a carrier portion which comprises or bears at least one epitope recognizable by at least one arm of said bi-specific antibody or antibody fragment. The targetable conjugate further comprises one or more therapeutic or diagnostic agents or enzymes. The invention provides constructs and methods for producing the bi-specific antibodies or antibody fragments, as well as methods for using them.

13 Claims, 5 Drawing Sheets

Schematic illustration of various Abs and bsAbs.

hMN14           734scFv hMN14Fab-734scFv           hMN14-734scFv

OTHER PUBLICATIONS

Stickney et al.; "Bifunctional Antibody: A Binary Radiopharmaceutical Delivery System for Imaging Colorectal Carcinoma,"; *Cancer Research*; vol. 51; Dec. 15, 1991; pp. 6650-6655.

Gautherot et al.; "Therapy for Colon Carcinoma Xenografts with Bispecific Antibody-Targeted, Iodine-131-Labeled Bivalent Hapten,"; *Cancer Supplement*; vol. 80; 1997; pp. 2618-2623.

Barbet et al.; "Radioimmunodetection of Medullary Thyroid Carcinoma Using Indium-111 Bivalent Hapten and Anti-CEA X Anti-DTPA-Indium,"; *The Journal of Nuclear Medicine*; vol. 39, No. 7; Jul. 1998.

Kranenborg et al.; "Development and Characterization of Anti-Renal Cell Carcinoma x Antichelate Bispecific Monoclonal Antibodies for Two-Phase Targeting of Renal Cell Carcinoma,"; *Cancer Research Supplement*; vol. 55; Dec. 1, 1995; pp. 5864s-5867s.

Schuhmacher et al.; "Multistep Tumor Targeting in Nude Mice Using Bispecific Antibodies and a Gallium Chelate Suitable for Immunoscintigraphy with Positron Emission Tomography,"; *Cancer Research*; vol. 55; Jan. 1, 1995; pp. 115-123.

Sharkey et al.; "Development of a Streptavidin—Anti-Carcinoembryonic Antigen Antibody, Radiolabeled Biotin Pretargeting Method For Radioimmunotherapy of Colorectal Cancer. Studies in A Colon Cancer Xenograft Model,"; *Bioconjugate Chemical*; vol. 8, No. 4; 1997.

K. Bosslet et al., "Generation of bispecific monoclonal antibodies for two phase radioimmunotherapy", Macmillan Press Ltd., British Journal of Cancer, (1991) 63/5, 681-686, XP-002120437.

Marion H.G.C. Kranenborg et al., "Development and Characterization of Anti-Renal Cell Carcinoma x Antichelate Bispecific Monoclonal Antibodies for Two-Phase Targeting of Renal Cell Carcinoma" Cancer Research, (Dec. 1995), 55 (23 Supp.), 5864S-5867S, XP-002120435.

Corine Manetti et al., "Intracellular Uptake and Catabolism of Anti-IgM Antibodies and Bi-Specific Antibody-Targeted Hapten by B-Lymphoma Cells", International Journal of Cancer, (1995), 63(2), 250-256, XP-002120770.

Manuel Bardies et al., "Bispecific Antibody and Iodine-131-Labeled Bivalent Hapten Dosimetry in Patients with Medullary Thyroid or Small-Cell Lung Cancer", Journal of Nuclear Medicine, vol. 37, (Nov. 1996), 1853-1859, XP-002116384.

J. Barbet et al., "Radioimmunotherapy of LS174T Colon Carcinoma in Nude Mice Using an Iodine-131-Labeled Bivalent Hapten Combined with An Anti-CEA x Anti-Indium-DTPA Bispecific Antibody", Tumor Biology, (Sep. 1997), vol. 18, No. Supp. 2, 31, XP-002120771.

Emmanuel Gautherot, "Therapy for Colon Carcinoma Xenografts with Bispecific Antibody-Targeted, Iodine-131-Labeled Bivalent Hapten", American Cancer Society, vol. 80, No. Supp. 12, (Dec. 1997), 2618-2623, XP-002110873.

Marion H.G.C. Kranenborg et al., "Two-Step Radio Immunotargeting of Renal-Cell Carcinoma Xenografts in Nude Mice with Anti-Renal-Cell-Carcinoma x Anti-DTPA Bispecific Monoclonal Antibodies", International Journal of Cancer, (Jan. 1998), 75 (1), 74-80, XP-002120436.

Francoise Kraeber-Bodere et al., "Phase I/II Trial of Two-Step Radioimmunotherapy in Medullary Thyroid Cancer (MTC) Using Bispecific Anti-CEA/Anti-DTPA-In Antibody and Iodine-131-Labeled Bivalent Hapten", Journal of Nuclear Medicine, (May 1998), vol. 39, No. 5 Supp., 246, XP-002120769.

Makoto Hosono et al., "Biodistribution and Dosimetric Study in Medullary Thyroid Cancer Xenograft Using Bispecific Antibody and Iodine-125-Labeled Bivalent Hapten", Journal of Nuclear Medicine, (Sep. 1998), 39 (9),1608-1613, XP-002120434.

Emmanuel Gautherot et al., "Delivery of Therapeutic Doses of Radioiodine Using Bispecific Antibody-Targeted Bivalent Haptens", Journal of Nuclear Medicine, (Nov. 1998), 39 (11),1937-1943, XP-002120432.

Francoise Kraeber-Bodere et al., "Bispecific Antibody and Bivalent Hapten Radioimmunotherapy in CEA-Producing Medullary Thyroid Cancer Xenograft", Journal of Nuclear Medicine, (Jan. 1990), 40 (1), 198-204, XP-002120433.

H. Karacay et al., "Studies on a humanized anti-CEA x murine anti-[In-DTPA] bispecific antibody construct for radioimmunotherapy of CEA-positive tumors", American Assoc. for Cancer Research Annual Meeting (Mar. 1999), vol. 40, 644, XP-002120429.

H. Karacay et al., "Pretargeting Studies with Humanized Anti-CEA x Murine Anti-[In-DTPA] Bispecific Antibody Construct and Tc-99M/ Re-188 Labeled Peptide", Journal of Nuclear Medicine, (May 1999), vol. 40, No. 5 Supp., 225, XP-002120430.

B.T. McGuinness et al., "Phage diabody repertoires for selection of large numbers of bispecific anitbody fragments," *Nature Biotechnology*, 14:1149-1154 (1996).

M. Alt et al., "Novel tetravalent and bispecific IgG-like antibody molecules combining single chain diabodies with the immunoglobulin gamma-1 or CH3 region," *FEBS LETT*, 454: 90-94 (1999).

T.B. Olafsen et al., "IgM secretory tailpiece drives multimerisation of bivalent scFv fragments in eukaryotic Cells," *Immunotechnology*, 4(2):141-153 (1998).

S.M. Kipriyanov et al., "Bispecific tandem diabody for tumor therapy with improved antigen binding and pharmacokinetics," *J. Mol. Biol.*, 293(1):41-56 (1999).

* cited by examiner

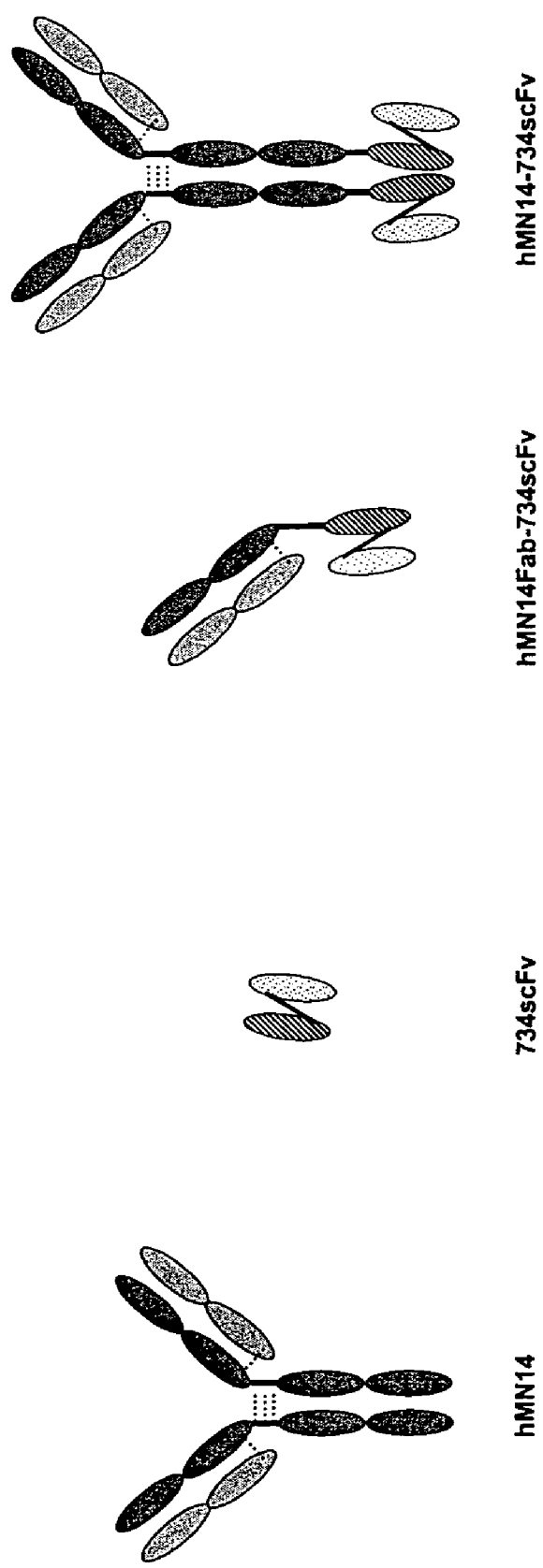
Figure 1. Schematic illustration of various Abs and bsAbs.

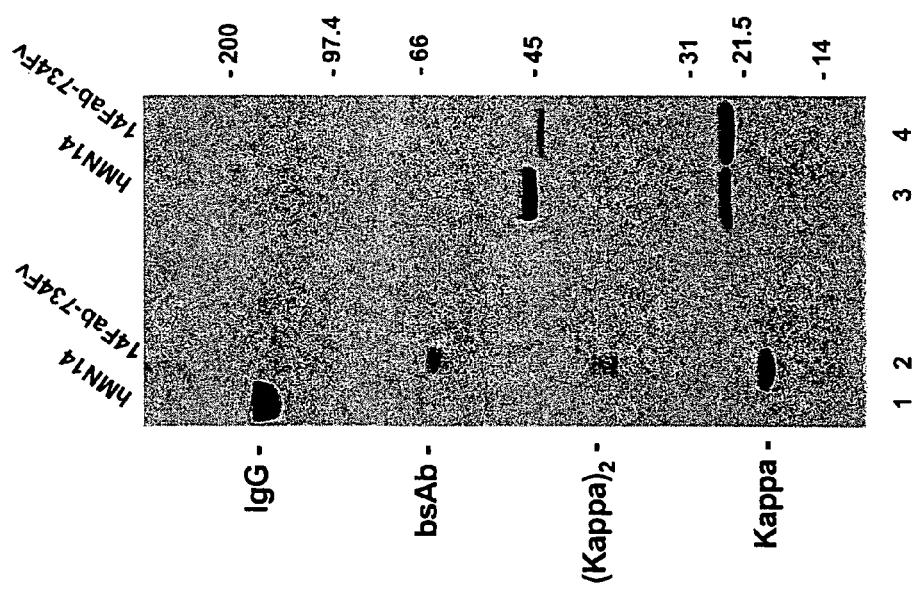
Figure 2. SDS-PAGE analysis of purified hMN14Fab-734scFv. 3 μg of hMN-14 IgG (lanes 1 and 3) or bsAb (lanes 2 and 4) was applied in each lane of a 4-20% polyacrylamide gel under non-reducing (lanes 1 and 2) and reducing (lanes 3 and 4) conditions.

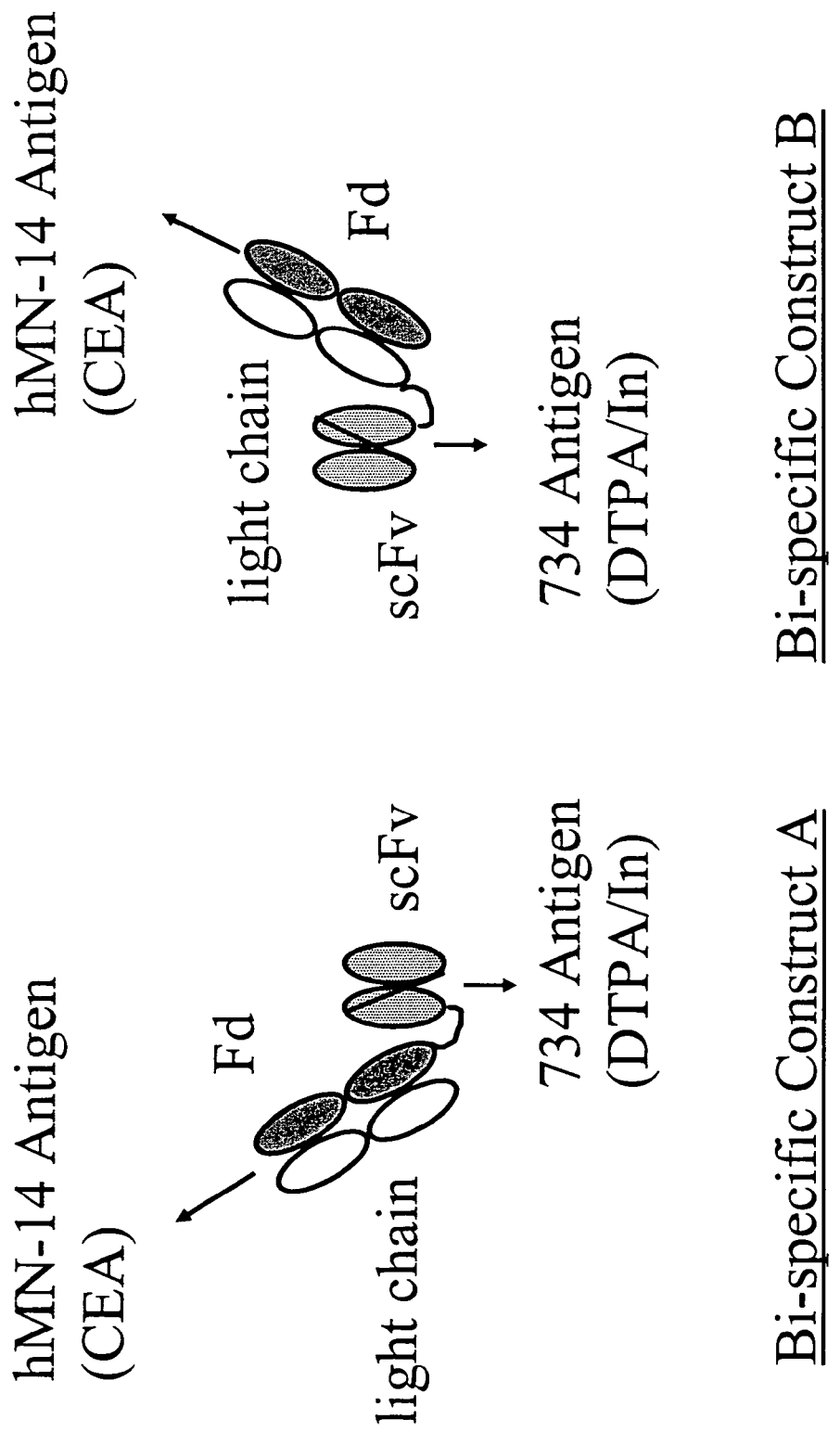
Figure 3. Schematic illustration of two bi-specific fusion proteins.

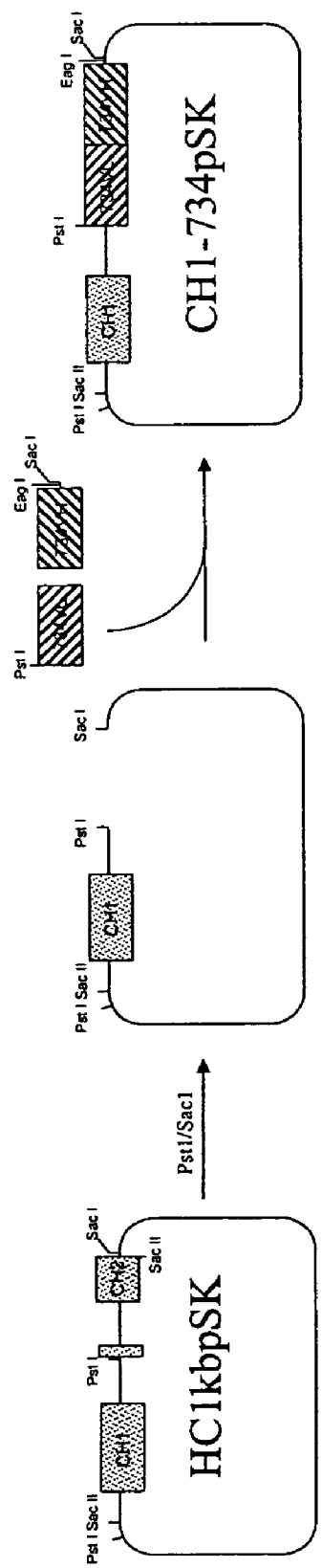
Figure 4. Schematic diagram illustrating production of a DNA construct useful for producing a hMN14Fab-734scFv bi-specific fusion proteins.

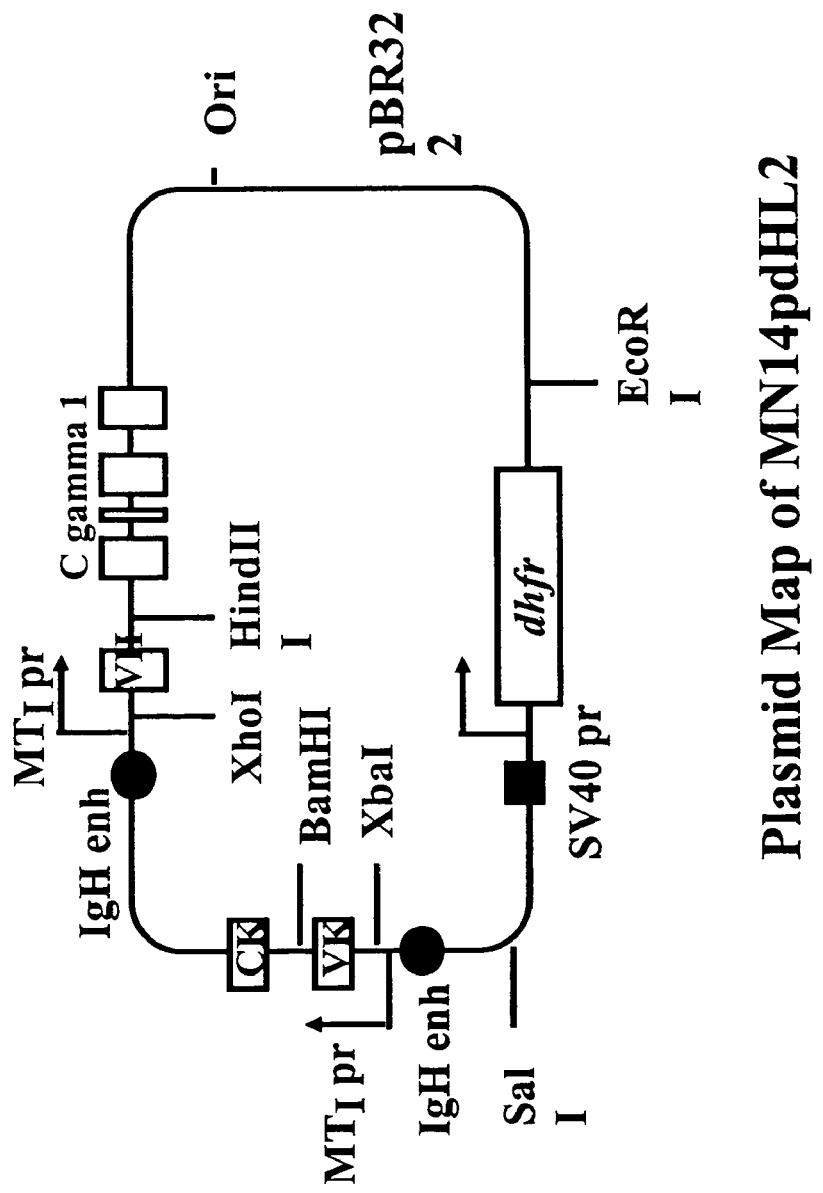
Figure 5. Schematic diagram illustrating production of a DNA construct useful for producing a hMN14Fab-734scFv bi-specific fusion protein.

ns

SEQUENCE LISTING

<160> NUMBER OF SEQ ID NOS: 14

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Phe Lys Tyr Lys
 1

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Gly Lys Tyr Cys
 1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (5)
<223> OTHER INFORMATION: Thiosemicarbazonylglyoxylcysteine (TscGCys)

<400> SEQUENCE: 3

Lys Tyr Lys Lys Cys
 1               5

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Ala Glu Tyr
 1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Cys Lys Tyr Lys
 1

<210> SEQ ID NO 6

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Gly Gly Ser
 1

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Gly Gly Gly Ser Gly Gly Gly Gly Ser Gly Gly Gly Gly Ser
 1               5                  10                  15

<210> SEQ ID NO 8
<211> LENGTH: 4
<212> TYPE: PRT
<213> ORGANISM: Homo sapiens

<400> SEQUENCE: 8

Pro Lys Ser Cys
 1

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Leu Val Val Thr Gln
 1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Thr Lys Leu Lys Ile Leu
 1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Gly Gly Gly Ser Gly Gly Gly Gly
 1               5
```

-continued

```
<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Gly Gly Gly Gly Ser
 1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Glu Val Lys Leu Gln Glu
 1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Thr Val Thr Val Ser Ser
 1               5
```

BI-SPECIFIC ANTIBODIES FOR PRE-TARGETING DIAGNOSIS AND THERAPY

This application is a continuation-in-part of U.S. Ser. No. 09/337,756, filed Jun. 22, 1999, the contents of which are incorporated herein by reference in their entirety.

BACKGROUND OF THE INVENTION

1. Field of the Invention

The invention relates to immunological reagents for therapeutic use, for example, in radioimmunotherapy (RAIT), and diagnostic use, for example, in radioimmunodiagnosis (RAID) and magnetic resonance imaging (MRI). In particular, the invention relates to bi-specific antibodies (bsAb) and bi-specific antibody fragments (bsFab) which have at least one arm that specifically binds a targeted tissue and at least one other arm that specifically binds a targetable conjugate. Further, the invention relates to monoclonal antibodies that have been raised against specific immunogens, humanized and chimeric monoclonal bi-specific antibodies and antibody fragments having at least one arm that specifically binds a targeted tissue and at least one other arm that specifically binds a targetable conjugate, DNAs that encode such antibodies and antibody fragments, and vectors for expressing the DNAs. Earlier provisional patent applications, U.S. Ser. No. 60/090,142 and U.S. Ser. No. 60/104,156 disclose a part of what is now included in this invention and are incorporated herein by reference in their entireties.

2. Related Art

An approach to cancer therapy and diagnosis involves directing antibodies or antibody fragments to disease tissues, wherein the antibody or antibody fragment can target a diagnostic agent or therapeutic agent to the disease site. One approach to this methodology which has been under investigation, involves the use of bi-specific monoclonal antibodies (bsAb) having at least one arm that specifically binds a targeted diseased tissue and at least one other arm that specifically binds a low molecular weight hapten. In this methodology, a bsAb is administered and allowed to localize to target, and to clear normal tissue. Some time later, a radiolabeled low molecular weight hapten is given, which being recognized by the second specificity of the bsAb, also localizes to the original target.

Although low MW haptens used in combination with bsAbs possess a large number of specific imaging and therapy uses, it is impractical to prepare individual bsAbs for each possible application. Further, the application of a bsAb/low MW hapten system has to contend with several other issues. First, the arm of the bsAb that binds to the low MW hapten must bind with high affinity, since a low MW hapten is designed to clear the living system rapidly, when not bound by bsAb. Second, the non-bsAb-bound low MW hapten actually needs to clear the living system rapidly to avoid non-target tissue uptake and retention. Third, the detection and/or therapy agent must remain associated with the low MW hapten throughout its application within the bsAb protocol employed.

Of interest with this approach are bsAbs that direct chelators and metal chelate complexes to cancers using Abs of appropriate dual specificity. The chelators and metal chelate complexes used are often radioactive, using radionuclides such as cobalt-57 (Goodwin et al., U.S. Pat. No. 4,863,713), indium-111 (Barbet et al., U.S. Pat. No. 5,256, 395 and U.S. Pat. No. 5,274,076, Goodwin et al., *J. Nucl. Med.*, 33:1366–1372 (1992), and Kranenborg et al., *Cancer Res* (suppl.), 55:5864s–5867s (1995) and *Cancer* (suppl.) 80:2390–2397 (1997)) and gallium-68 (Boden et al., *Bioconjugate Chem.*, 6:373–379, (1995) and Schuhmacher et al., *Cancer Res.*, 55:115–123 (1995)) for radioimmunoimaging. Because the Abs were raised against the chelators and metal chelate complexes, they have remarkable specificity for the complex against which they were originally raised. Indeed, the bsAbs of Boden et al. have specificity for single enantiomers of enantiomeric mixtures of chelators and metal-chelate complexes. This great specificity has proven to be a disadvantage in one respect, in that other nuclides such as yttrium-90 and bismuth-213 useful for radioimmunotherapy (RAIT), and gadolinium useful for MRI, cannot be readily substituted into available reagents for alternative uses. As a result iodine-131, a non-metal, has been adopted for RAIT purposes by using an I-131-labeled indium-metal-chelate complex in the second targeting step. A second disadvantage to this methodology requires that antibodies be raised against every agent desired for diagnostic or therapeutic use.

Thus, there is a continuing need for an immunological agent which can be directed to diseased tissue and can specifically bind to a subsequently administered targetable diagnostic or therapeutic conjugate.

OBJECTS OF THE INVENTION

It is one object of the present invention to provide a bi-specific antibody or antibody fragment having at least one arm that specifically binds a targeted tissue and at least one other arm that specifically binds a targetable conjugate that can be modified for use in a wide variety of diagnostic and therapeutic applications.

Other objects of the invention are to provide pre-targeting methods of diagnosis and therapy using the combination of bi-specific antibody and targetable conjugate, methods of making the bi-specifics, and kits for use in such methods.

In accomplishing the foregoing object, the present inventors have discovered that it is advantageous to raise bsAbs against a targetable conjugate that is capable of carrying one or more diagnostic or therapeutic agents. By utilizing this technique, the characteristics of the chelator, metal chelate complex, therapeutic agent or diagnostic agent can be varied to accommodate differing applications, without raising new bsAbs for each new application. Further, by using this approach, two or more distinct chelators, metal chelate complexes or therapeutic agents can be used with the inventive bsAb.

SUMMARY OF THE INVENTION

The present invention relates to a bi-specific antibody or antibody fragment having at least one arm that specifically binds a targeted tissue and at least one other arm that specifically binds a targetable conjugate.

In one embodiment, the invention provides a method of treating or identifying diseased tissues in a patient, comprising:

(A) administering to the patient a bi-specific antibody or antibody fragment having at least one arm that specifically binds a targeted tissue and at least one other arm that specifically binds a targetable conjugate;

(B) optionally, administering to the patient a clearing composition, and allowing the composition to clear non-localized antibodies or antibody fragments from circulation;

(C) administering to the patient a first targetable conjugate which comprises a carrier portion which comprises or bears at least one epitope recognizable by the at least one other arm of the bi-specific antibody or antibody fragment, and one or more conjugated therapeutic or diagnostic agents, or enzymes; and (D) when the targetable conjugate comprises an enzyme, further administering to the patient
   1) a prodrug, when the enzyme is capable of converting the prodrug to a drug at the target site; or
   2) a drug which is capable of being detoxified in the patient to form an intermediate of lower toxicity, when the enzyme is capable of reconverting the detoxified intermediate to a toxic form, and, therefore, of increasing the toxicity of the drug at the target site, or
   3) a prodrug which is activated in the patient through natural processes and is subject to detoxification by conversion to an intermediate of lower toxicity, when the enzyme is capable of reconverting the detoxified intermediate to a toxic form, and, therefore, of increasing the toxicity of the drug at the target site, or
   4) a second targetable conjugate which comprises a carrier portion which comprises or bears at least one epitope recognizable by the at least one other arm of the bi-specific antibody or antibody fragment, and a prodrug, when the enzyme is capable of converting the prodrug to a drug at the target site.

In another embodiment, the invention provides a kit useful for treating or identifying diseased tissues in a patient comprising:

(A) a bi-specific antibody or antibody fragment having at least one arm that specifically binds a targeted tissue and at least one other arm that specifically binds a targetable conjugate;

(B) a first targetable conjugate which comprises a carrier portion which comprises or bears at least one epitope recognizable by the at least one other arm of the bi-specific antibody or antibody fragment, and one or more conjugated therapeutic or diagnostic agents, or enzymes; and (C) optionally, a clearing composition useful for clearing non-localized antibodies and antibody fragments; and (D) optionally, when the first targetable conjugate comprises an enzyme,
   1) a prodrug, when the enzyme is capable of converting the prodrug to a drug at the target site; or
   2) a drug which is capable of being detoxified in the patient to form an intermediate of lower toxicity, when the enzyme is capable of reconverting the detoxified intermediate to a toxic form, and, therefore, of increasing the toxicity of the drug at the target site, or
   3) a prodrug which is activated in the patient through natural processes and is subject to detoxification by conversion to an intermediate of lower toxicity, when the enzyme is capable of reconverting the detoxified intermediate to a toxic form, and, therefore, of increasing the toxicity of the drug at the target site, or
   4) a second targetable conjugate which comprises a carrier portion which comprises or bears at least one epitope recognizable by the at least one other arm of the bi-specific antibody or antibody fragment, and a prodrug, when the enzyme is capable of converting the prodrug to a drug at the target site.

Another embodiment of the invention is to provide DNA constructs which encode such antibodies or antibody fragments. Specifically, DNA constructs which produce the variable regions which provide the advantageous properties of reactivity to a targetable conjugate and reactivity to a disease tissue. In accordance with this aspect of the present invention, there is provided a recombinant DNA construct comprising an expression cassette capable of producing in a host cell a bi-specific antibody or antibody fragment having at least one arm that specifically binds a targeted tissue and at least one other arm that specifically binds a targetable conjugate, wherein the construct comprises, in the 5' to 3' direction of transcription, a transcriptional initiation regulatory region functional in the host cell, a translational initiation regulatory region functional in the host cell, a DNA sequence encoding the bi-specific antibody or antibody fragment, and a transcriptional and translational termination regulatory region functional in the host cell, wherein the bi-specific antibody or antibody fragment is under the control of the regulatory regions.

Another embodiment of the invention provides a method of preparing the antibodies or antibody fragments by recombinant technology. In accordance with this aspect of the present invention, there is provided a method of preparing a bi-specific antibody or antibody fragment having at least one arm that specifically binds a targeted tissue and at least one other arm that specifically binds a targetable conjugate, comprising:

(A) introducing the recombinant DNA construct described above into a host cell;

(B) growing the cell and isolating the antibody or antibody fragment.

In another embodiment of the present invention there is provided a method of preparing a bi-specific fusion protein having at least one arm that specifically binds to a targeted tissue and at least one other arm that is specifically binds to a targetable conjugate, comprising:

(1) (A) introducing into a host cell a recombinant DNA construct comprising an expression cassette capable of producing in the host cell a fragment of the bi-specific fusion protein, wherein the construct comprises, in the 5' to 3' direction of transcription, a transcriptional initiation regulatory region functional in the host cell, a translational initiation regulatory region functional in the host cell, a DNA sequence encoding a scFv linked to a light-chain antibody fragment, and a transcriptional and translational termination regulatory region functional in the host cell, wherein the fragment of the bi-specific fusion protein is under the control of the regulatory regions;

(B) co-introducing into the host cell a recombinant DNA construct comprising an expression cassette capable of producing in the host cell a Fd fragment which is complementary to the light-chain antibody fragment in (A) and which when associated with the light-chain antibody fragment forms a Fab fragment whose binding site is specific for the targeted tissue, wherein the construct comprises, in the 5' to 3' direction of transcription, a transcriptional initiation regulatory region functional in the host cell, a translational initiation regulatory region functional in the host cell, a DNA sequence encoding a Fd fragment, and a transcriptional and translational termination regulatory region functional in the host cell, wherein the Fd fragment is under the control of the regulatory regions;

(C) growing the cell and isolating the bi-specific fusion protein, or (2) (A) introducing into a first host cell a recombinant DNA construct comprising an expression cassette capable of producing in the first host cell a fragment of the bi-specific fusion protein, wherein the construct comprises, in the 5' to 3' direction of transcription, a transcriptional initiation regulatory region functional in the first host cell, a translational initiation regulatory region functional in the first host cell, a DNA sequence encoding a scFv linked to a light-chain antibody fragment, and a transcriptional and translational termination regulatory region functional in the first host cell, wherein the fragment of the bi-specific fusion protein is under the control of the regulatory regions;

(B) introducing into a second host cell a recombinant DNA construct comprising an expression cassette capable of producing in the second host cell a Fd fragment which is complementary to the light-chain antibody fragment in (2)(A) and which when associated with the light-chain antibody fragment forms a Fab fragment whose binding site is specific for the targeted tissue, wherein the construct comprises, in the 5' to 3' direction of transcription, a transcriptional initiation regulatory region functional in the second host cell, a translational initiation regulatory region functional in the second host cell, a DNA sequence encoding a Fd fragment, and a transcriptional and translational termination regulatory region functional in the second host cell, wherein the Fd fragment is under the control of the regulatory regions;

(C) growing the first and second host cells;

(D) optionally isolating the bi-specific fusion protein fragment and the Fd fragment; and (E) combining the fragments to produce a bi-specific fusion protein and isolating the bi-specific fusion protein.

A variety of host cells can be used to prepare bi-specific antibodies or antibody fragments, including, but not limited to, mammalian cells, insect cells, plant cells and bacterial cells. In one embodiment, the method utilizes a mammalian zygote, and the introduction of the recombinant DNA construct produces a transgenic animal capable of producing a bi-specific antibody or antibody fragment.

A further embodiment of the invention involves using the inventive antibody or antibody fragment in photodynamic therapy.

A further embodiment of the invention involves using the inventive antibody or antibody fragment in radioimmunoimaging for positron-emission tomography (PET).

A further embodiment of the invention involves using the inventive antibody or antibody fragment in radioimmunoimaging for single photon emission.

A further embodiment of the invention involves using the inventive antibody or antibody fragment in magnetic resonance imaging (MRI).

A further embodiment of the invention involves using the inventive antibody or antibody fragment in boron neutron capture therapy (BNCT).

Additional aspects, features and advantages of the invention will be set forth in the description which follows, and in part will be obvious from the description, or may be learned by practice of the invention. The embodiments and advantages of the invention may be realized and obtained by means of the instrumentalities and combinations particularly pointed out in the appended claims.

BRIEF DESCRIPTION OF THE DRAWINGS

FIG. 1 schematically illustrates various Abs and bsAbs.

FIG. 2 provides SDS-PAGE analysis of purified hMN14Fab-734scFv.

FIG. 3 schematically illustrates two bi-specific fusion proteins.

FIG. 4 illustrates the production of a DNA construct useful for producing a hMN14Fab-734scFv bi-specific fusion protein.

FIG. 5 illustrates the production of a DNA construct useful for producing a hMN14Fab-734scFv bi-specific fusion protein.

DETAILED DESCRIPTION OF PREFERRED EMBODIMENTS

The present invention provides a bi-specific antibody or antibody fragment having at least one arm that specifically binds a targeted tissue and at least one other arm that specifically binds a targetable conjugate. The targetable conjugate comprises a carrier portion which comprises or bears at least one epitope recognized by at least one arm of the bi-specific antibody or antibody fragment. In a preferred embodiment, the epitope is a hapten. In an alternative embodiment, the epitope is a part of the carrier. Examples of recognizable haptens include, but are not limited to, chelators, such as DTPA, fluorescein isothiocyanate, vitamin B-12 and other moieties to which specific antibodies can be raised. The carrier portion also may be conjugated to a variety of agents useful for treating or identifying diseased tissue. Examples of conjugated agents include, but are not limited to, metal chelate complexes, drugs, toxins and other effector molecules, such as cytokines, lymphokines, chemokines, immunomodulators, radiosensitizers, asparaginase, carboranes and radioactive halogens. Additionally, enzymes useful for activating a prodrug or increasing the target-specific toxicity of a drug can be conjugated to the carrier. Thus, the use of bsAb which have at least one arm that specifically binds a targetable conjugate allows a variety of therapeutic and diagnostic applications to be performed without raising new bsAb for each application.

The present invention encompasses antibodies and antibody fragments. The antibody fragments are antigen binding portions of an antibody, such as $F(ab')_2$, $F(ab)_2$, Fab', Fab, and the like. The antibody fragments bind to the same antigen that is recognized by the intact antibody. For example, an anti-CD22 monoclonal antibody fragment binds to an epitope of CD22. The bsAb of the present invention include, but are not limited to, IgG×IgG, IgG×F(ab')$_2$, IgG×Fab', IgG×scFv, F(ab')$_2$×F(ab')$_2$, Fab'×F(ab')$_2$, Fab'×Fab', Fab'×scFv and scFv×scFv bsmabs. Also, species such as scFv×IgG×scFv and Fab'×IgG×Fab', scFv×F(ab')$_2$×scFv and Fab'×F(ab')$_2$×Fab' are included. Most preferably, site-specific attachment sites on the IgG or F(ab')$_2$ of one or both mabs can be utilized, such as an engineered carbohydrate or an engineered or liberated free thiol group. Since these mabs are dimeric they can be coupled with two moles of the second mab. For instance, anti-CEA F(ab')$_2$ mAb having engineered light-chain carbohydrate can be oxidized and converted using a hydrazide-maleimide cross-linker to a derivatized anti-CEA F(ab')$_2$ having at least one pendant maleimide group per each light chain. This species is coupled to an anti-chelate Fab'-SH at a 1:2 molar ratio, at least, such that an anti-chelate-Fab'×anti-CEA-F(ab')$_2$-anti-chelate Fab' conjugate is produced. The resultant bsAb is bivalent with respect to the target tissue and the targetable conjugate. It is further understood that the use of the term "bsAb" in the present disclosure encompasses bi-specific monoclonal antibodies and antibody fragments.

The term "antibody fragment" also includes any synthetic or genetically engineered protein that acts like an antibody by binding to a specific antigen to form a complex. For example, antibody fragments include isolated fragments, "Fv" fragments, consisting of the variable regions of the heavy and light chains, recombinant single chain polypeptide molecules in which light and heavy chain variable regions are connected by a peptide linker ("sFv proteins"), and minimal recognition units consisting of the amino acid residues that mimic the hypervariable region.

The targetable conjugate can be of diverse structure, but is selected not only to elicit sufficient immune responses, but also for rapid in vivo clearance when used within the bsAb targeting method. Hydrophobic agents are best at eliciting strong immune responses, whereas hydrophilic agents are preferred for rapid in vivo clearance, thus, a balance between hydrophobic and hydrophilic needs to be established. This may be accomplished in a preferred approach, in part, by relying on the use of hydrophilic chelating agents to offset the inherent hydrophobicity of many organic moieties. Also, sub-units of the targetable conjugate may be chosen which have opposite solution properties, for example, peptides, which contain amino acids, some of which are hydrophobic and some of which are hydrophilic. Aside from peptides, carbohydrates may be used. Additionally, the targetable conjugate can comprise PEG derivatives to increase its circulation time in a patient.

Carriers having as few as one amine residue may be used, preferably two to ten amino acid residues, if also coupled to other moieties such as chelating agents. Examples include modified amino acids, such as bis-DTPA-lysine, and bis-DTPA-diamine. These agents can be linked covalently to molecules which are to be targeted. The hapten moiety of the carrier portion should be a low molecular weight conjugate, preferably having a molecular weight of 100,000 daltons or less, and advantageously less than about 20,000 daltons, 10,000 daltons or 5,000 daltons, including the metal ions in the chelates. For instance, the known peptide di-indium-DTPA-Tyr-Lys(DTPA)-OH has been used to generate antibodies against the indium-DTPA portion of the molecule. However, by use of the non-indium-containing molecule, and appropriate screening steps, new Abs against the tyrosyl-lysine dipeptide can be made. More usually, the antigenic peptide will have four or more residues, such as the peptide Ac-Phe-Lys(DTPA)-Tyr-Lys(DTPA)-NH$_2$ (SEQ ID NO: 1). Again, the non-metal-containing peptide is used as an immunogen, with resultant Abs screened for reactivity against the Phe-Lys-Tyr-Lys (SEQ ID NO: 1) backbone.

In one embodiment, unnatural amino acids, e.g., D-amino acids, are incorporated into the backbone structure to ensure that, when used with the final bsAb/targetable conjugate system, the arm of the bsAb which recognizes the targetable conjugate is completely specific.

In a preferred embodiment, the immunogen used has repeating units, resulting in retention of bivalency when used in the final bsAb/targetable conjugate system. Such an immunogen is a peptide of the formula X-Gly-D-Tyr-D-trp-Gly-D-Lys(X)-Gly-D-Tyr-D-Trp-OH, wherein the X-residues are free amino groups which can be substituted later with chelates. X can also represent a moiety selected from the group consisting of a protected amino acid group, a chelating agent and a metal-chelate complex. Thiol groups also may be used for later chelate coupling, in lieu of amino groups, by incorporating cysteinyl-residues into the immunogenic peptide, for example, Ac-Cys(Y)-D-Tyr-D-Trp-Gly-D-Cys(Y)-Gly-D-Tyr-D-Trp-OH, wherein -Y- is a free thiol group. Y can also represent a moiety selected from the group consisting of a protected thiol group, a thiol-linked chelating agent and a metal-chelate complex. The cleaved peptide containing methyl-derivatized thiol groups is for the production of antibodies. Later, the peptide may be prepared with removable protecting groups, such as trityl or acetamidomethyl, for chelate substitution reactions.

The peptides to be used as immunogens are synthesized conveniently on an automated peptide synthesizer using a solid-phase support and standard techniques of repetitive orthogonal deprotection and coupling. Free amino groups in the peptide, that are to be used later for chelate conjugation, are advantageously blocked with small organic moieties, for example by acetylation. For instance, Ac-Gly-D-Tyr-D-Trp-Gly-D-Lys(Ac)-Gly-D-Tyr-D-Trp-OH, cleaved from its assembly resin is then activated through its single carboxyl moiety using active ester/anhydride methodology and coupled in multiple units to KLH. For immunogenic use, the di-cysteinyl-containing peptide Ac-Cys(Y)-D-Tyr-D-Trp-Gly-D-Cys(Y)-Gly-D-Tyr-D-Trp-OH can be removed from the resin with the thiol groups protected by methylation to generate Ac-Cys(Me)-D-Tyr-D-Trp-Gly-D-Cys(Me)-Gly-D-Tyr-D-Trp-OH. This can then be activated for KLH coupling using the same standard methods. When the peptides are prepared for later use within the bsAb system, they are advantageously cleaved from the resins to generate the corresponding C-terminal amides, in order to inhibit in vivo carboxypeptidase activity.

According to one embodiment of the invention, the targetable conjugate can encompass a carbohydrate. Suitable such carbohydrates include carbohydrate chains of two to six sugar units long. The targetable conjugate also can comprise a polymeric carbohydrate, such as dextran.

In another embodiment of the invention, the haptens of the targetable conjugate comprise a known immunogenic recognition moiety, for example, a known hapten. Using a known hapten, for example, fluorescein isothiocyanate (FITC), higher specificity of the targetable conjugate for the antibody is exhibited. This occurs because antibodies raised to the hapten are known and can be incorporated into the inventive antibody. Thus, binding of the targetable conjugate with the attached chelator or metal-chelate complex would be highly specific for the inventive antibody or antibody fragment. Another example of a hapten to be substituted onto the targetable conjugate includes vitamin B12. The use of vitamin B12 is advantageous since anti-B12 Mabs are known and no free serum B12 exists, therefore, great specificity for the antibody may be exhibited. An example of a targetable conjugate containing a hapten includes Ac-Cys-(S-Bz-DTPA)-Gly-Lys-(N-FITC)-Tyr-Cys-(S-Bz-DTPA) NH$_2$ (SEQ ID NO: 2). The chelator or its chelate with a metal cation also can function as the hapten to which an antibody is raised. Another example of a hapten to be conjugated to a targetable conjugate includes biotin.

In a further preferred embodiment, a radionuclide used for imaging and/or therapy may be integrated into the design of the original immunogen. For instance, Ac-Gly-D-iodo-Tyr-D-Trp-Gly-D-Lys(Ac)-Gly-D-iodo-Tyr-D-Trp-OH is used as an immunogen with the express purpose of raising an antibody which is reactive with an iodine-containing peptide, but not with the non-iodo version of the same peptide, namely Ac-Gly-D-Tyr-D-Trp-Gly-D-Lys(Ac)-Gly-D-Tyr-D-Trp-OH. Specificity of Abs for the former over the latter can be demonstrated using standard screening techniques. Of particular importance within this embodiment is the use of astatine-substituted peptides as immunogens to generate Abs and thus bsAb which recognize peptides substituted with alpha-particle-emitting astatine nuclides for RAIT. In other embodiments, any halogen can be integrated into the design of the original immunogen, including, for example, fluorine-18, bromine, and nuclides of iodine, for example, iodine-124 and iodine-123. Similarly, other non metals can be used, for example $^{32}P$, $^{33}P$ and $^{35}S$.

New Abs to peptide backbones are generated by well-known methods for Ab production. For example, injection of an immunogen, such as (peptide)$_n$-KLH (n=1–30) in complete Freund's adjuvant, followed by two subsequent injections of the same immunogen suspended in incomplete Freund's adjuvant into immunocompetent animals, is followed three days after an i.v. boost of antigen, by spleen cell harvesting. Harvested spleen cells are then fused with Sp2/0-Ag14 myeloma cells and culture supernatants of the resulting clones analyzed for anti-peptide reactivity using a direct-binding ELISA. Fine specificity of generated Abs can be analyzed for by using peptide fragments of the original immunogen. These fragments can be prepared readily using an automated peptide synthesizer. For Ab production, enzyme-deficient hybridomas are isolated to enable selection of fused cell lines. This technique also can be used to raise antibodies to one or more of the chelates comprising the targetable conjugate, e.g., In(III)-DTPA chelates. Monoclonal mouse antibodies to an In(III)-di-DTPA are known (Barbet '395 supra).

After the initial raising of antibodies to the immunogen, the antibodies can be sequenced and subsequently prepared by recombinant techniques. Humanization and chimerization of murine antibodies and antibody fragments are well known to those skilled in the art. For example, humanized monoclonal antibodies are produced by transferring mouse complementary determining regions from heavy and light variable chains of the mouse immunoglobulin into a human variable domain, and then, substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by the publication of Orlandi et al., *Proc. Nat'l Acad. Sci. USA* 86: 3833 (1989), which is incorporated by reference in its entirety. Techniques for producing humanized Mabs are described, for example, by Jones et al., *Nature* 321: 522 (1986), Riechmann et al., *Nature* 332: 323 (1988), Verhoeyen et al., *Science* 239: 1534 (1988), Carter et al., *Proc. Nat'l Acad. Sci. USA* 89: 4285 (1992), Sandhu, *Crit. Rev. Biotech.* 12: 437 (1992), and Singer et al., *J. Immun.* 150: 2844 (1993), each of which is hereby incorporated by reference.

Alternatively, fully human antibodies can be obtained from transgenic non-human animals. See, e.g., Mendez et al., *Nature Genetics*, 15: 146–156 (1997); U.S. Pat. No. 5,633,425. For example, human antibodies can be recovered from transgenic mice possessing human immunoglobulin loci. The mouse humoral immune system is humanized by inactivating the endogenous immunoglobulin genes and introducing human immunoglobulin loci. The human immunoglobulin loci are exceedingly complex and comprise a large number of discrete segments which together occupy almost 0.2% of the human genome. To ensure that transgenic mice are capable of producing adequate repertoires of antibodies, large portions of human heavy- and light-chain loci must be introduced into the mouse genome. This is accomplished in a stepwise process beginning with the formation of yeast artificial chromosomes (YACs) containing either human heavy- or light-chain immunoglobulin loci in germline configuration. Since each insert is approximately 1 Mb in size, YAC construction requires homologous recombination of overlapping fragments of the immunoglobulin loci. The two YACs, one containing the heavy-chain loci and one containing the light-chain loci, are introduced separately into mice via fusion of YAC-containing yeast spheroblasts with mouse embryonic stem cells. Embryonic stem cell clones are then microinjected into mouse blastocysts. Resulting chimeric males are screened for their ability to transmit the YAC through their germline and are bred with mice deficient in murine antibody production. Breeding the two transgenic strains, one containing the human heavy-chain loci and the other containing the human light-chain loci, creates progeny which produce human antibodies in response to immunization.

Unrearranged human immunoglobulin genes also can be introduced into mouse embryonic stem cells via microcell-mediated chromosome transfer (MMCT). See, e.g., Tomizuka et al., *Nature Genetics*, 16: 133 (1997). In this methodology microcells containing human chromosomes are fused with mouse embryonic stem cells. Transferred chromosomes are stably retained, and adult chimeras exhibit proper tissue-specific expression.

As an alternative, an antibody or antibody fragment of the present invention may be derived from human antibody fragments isolated from a combinatorial immunoglobulin library. See, e.g., Barbas et al., *METHODS: A Companion to Methods in Enzymology* 2: 119 (1991), and Winter et al., *Ann. Rev. Immunol.* 12: 433 (1994), which are incorporated by reference. Many of the difficulties associated with generating monoclonal antibodies by B-cell immortalization can be overcome by engineering and expressing antibody fragments in *E. coli*, using phage display. To ensure the recovery of high affinity, monoclonal antibodies a combinatorial immunoglobulin library must contain a large repertoire size. A typical strategy utilizes mRNA obtained from lymphocytes or spleen cells of immunized mice to synthesize cDNA using reverse transcriptase. The heavy- and light-chain genes are amplified separately by PCR and ligated into phage cloning vectors. Two different libraries are produced, one containing the heavy-chain genes and one containing the light-chain genes. Phage DNA is islolated from each library, and the heavy- and light-chain sequences are ligated together and packaged to form a combinatorial library. Each phage contains a random pair of heavy- and light-chain cDNAs and upon infection of *E. coli* directs the expression of the antibody chains in infected cells. To identify an antibody that recognizes the antigen of interest, the phage library is plated, and the antibody molecules present in the plaques are transferred to filters. The filters are incubated with radioactively labeled antigen and then washed to remove excess unbound ligand. A radioactive spot on the autoradiogram identifies a plaque that contains an antibody that binds the antigen. Cloning and expression vectors that are useful for producing a human immunoglobulin phage library can be obtained, for example, from STRATAGENE Cloning Systems (La Jolla, Calif.).

A similar strategy can be employed to obtain high-affinity scFv. See, e.g., Vaughn et al., *Nat. Biotechnol.*, 14: 309–314 (1996). An scFv library with a large repertoire can be constructed by isolating V-genes from non-immunized human donors using PCR primers corresponding to all known $V_H$, $V_\kappa$ and $V_\lambda$ gene families. Following amplification, the $V_\kappa$ and $V_\lambda$ pools are combined to form one pool. These fragments are ligated into a phagemid vector. The scFv linker, (Gly$_4$, Ser)$_3$, is then ligated into the phagemid upstream of the $V_L$ fragment. The $V_H$ and linker-$V_L$ fragments are amplified and assembled on the $J_H$ region. The resulting $V_H$-linker-$V_L$ fragments are ligated into a phagemid vector. The phagemid library can be panned using filters, as described above, or using immunotubes (Nunc;

Maxisorp). Similar results can be achieved by constructing a combinatorial immunoglobulin library from lymphocytes or spleen cells of immunized rabbits and by expressing the scFv constructs in P. pastoris. See, e.g., Ridder et al., Biotechnology, 13: 255–260 (1995). Additionally, following isolation of an appropriate scFv, antibody fragments with higher binding affinities and slower dissociation rates can be obtained through affinity maturation processes such as CDR3 mutagenesis and chain shuffling. See, e.g., Jackson et al., Br. J. Cancer, 78: 181–188 (1998); Osbourn et al., Immunotechnology, 2: 181–196 (1996).

The bsAb can be prepared by techniques known in the art, for example, an anti-CEA tumor Ab and an anti-peptide Ab are both separately digested with pepsin to their respective $F(ab')_2$s. The anti-CEA-Ab-$F(ab')_2$ is reduced with cysteine to generate Fab' monomeric units which are further reacted with the cross-linker bis(maleimido) hexane to produce Fab'-maleimide moieties. The anti-peptide Ab-$F(ab')_2$ is reduced with cysteine and the purified, recovered anti-peptide Fab'-SH reacted with the anti-CEA-Fab'-maleimide to generate the Fab'×Fab' bi-specific Ab. Alternatively, the anti-peptide Fab'-SH fragment may be coupled with the anti-CEA $F(ab')_2$ to generate a $F(ab')_2$×Fab' construct, or with anti-CEA IgG to generate an IgG×Fab' bi-specific construct. In one embodiment, the IgG×Fab' construct can be prepared in a site-specific manner by attaching the antipeptide Fab' thiol group to anti-CEA IgG heavy-chain carbohydrate which has been periodate-oxidized, and subsequently activated by reaction with a commercially available hydrazide-maleimide cross-linker. The component Abs used can be chimerized or humanized by known techniques. A chimeric antibody is a recombinant protein that contains the variable domains and complementary determining regions derived from a rodent antibody, while the remainder of the antibody molecule is derived from a human antibody. Humanized antibodies are recombinant proteins in which murine complementarity determining regions of a monoclonal antibody have been transferred from heavy and light variable chains of the murine immunoglobulin into a human variable domain.

A variety of recombinant methods can be used to produce bi-specific antibodies and antibody fragments. For example, bi-specific antibodies and antibody fragments can be produced in the milk of transgenic livestock. See, e.g., Colman, A., Biochem. Soc. Symp., 63: 141–147, 1998; U.S. Pat. No. 5,827,690. Two DNA constructs are prepared which contain, respectively, DNA segments encoding paired immunoglobulin heavy and light chains. The fragments are cloned into expression vectors which contain a promoter sequence that is preferentially expressed in mammary epithelial cells. Examples include, but are not limited to, promoters from rabbit, cow and sheep casein genes, the cow α-lactoglobulin gene, the sheep β-lactoglobulin gene and the mouse whey acid protein gene. Preferably, the inserted fragment is flanked on its 3' side by cognate genomic sequences from a mammary-specific gene. This provides a polyadenylation site and transcript-stabilizing sequences. The expression cassettes are coinjected into the pronuclei of fertilized, mammalian eggs, which are then implanted into the uterus of a recipient female and allowed to gestate. After birth, the progeny are screened for the presence of both transgenes by Southern analysis. In order for the antibody to be present, both heavy and light chain genes must be expressed concurrently in the same cell. Milk from transgenic females is analyzed for the presence and functionality of the antibody or antibody fragment using standard immunological methods known in the art. The antibody can be purified from the milk using standard methods known in the art.

A chimeric Ab is constructed by ligating the cDNA fragment encoding the mouse light variable and heavy variable domains to fragment encoding the C domains from a human antibody. Because the C domains do not contribute to antigen binding, the chimeric antibody will retain the same antigen specificity as the original mouse Ab but will be closer to human antibodies in sequence. Chimeric Abs still contain some mouse sequences, however, and may still be immunogenic. A humanized Ab contains only those mouse amino acids necessary to recognize the antigen. This product is constructed by building into a human antibody framework the amino acids from mouse complementarity determining regions.

Other recent methods for producing bsAbs include engineered recombinant Abs which have additional cysteine residues so that they crosslink more strongly than the more common immunoglobulin isotypes. See, e.g., FitzGerald et al., Protein Eng. 10(10): 1221–1225, 1997. Another approach is to engineer recombinant fusion proteins linking two or more different single-chain antibody or antibody fragment segments with the needed dual specificities. See, e.g., Coloma et al., Nature Biotech. 15:159–163, 1997. A variety of bi-specific fusion proteins can be produced using molecular engineering. In one form, the bi-specific fusion protein is monovalent, consisting of, for example, a scFv with a single binding site for one antigen and a Fab fragment with a single binding site for a second antigen. In another form, the bi-specific fusion protein is divalent, consisting of, for example, an IgG with two binding sites for one antigen and two scFv with two binding sites for a second antigen.

Functional bi-specific single-chain antibodies (bscAb), also called diabodies, can be produced in mammalian cells using recombinant methods. See, e.g., Mack et al., Proc. Natl. Acad. Sci., 92: 7021–7025, 1995. For example, bscAb are produced by joining two single-chain Fv fragments via a glycine-serine linker using recombinant methods. The V light-chain ($V_L$) and V heavy-chain ($V_H$) domains of two antibodies of interest are isolated using standard PCR methods. The $V_L$ and $V_H$ cDNA's obtained from each hybridoma are then joined to form a single-chain fragment in a two-step fusion PCR. The first PCR step introduces the $(Gly_4-Ser_1)_3$ linker, and the second step joins the $V_L$ and $V_H$ amplicons. Each single chain molecule is then cloned into a bacterial expression vector. Following amplification, one of the single-chain molecules is excised and sub-cloned into the other vector, containing the second single-chain molecule of interest. The resulting bscAb fragment is subcloned into an eukaryotic expression vector. Functional protein expression can be obtained by transfecting the vector into chinese hamster ovary cells. Bi-specific fusion proteins are prepared in a similar manner. Bi-specific single-chain antibodies and bi-specific fusion proteins are included within the scope of the present invention.

Bi-specific fusion proteins linking two or more different single-chain antibodies or antibody fragments are produced in similar manner. Recombinant methods can be used to produce a variety of fusion proteins. For example a fusion protein comprising a Fab fragment derived from a humanized monoclonal anti-CEA antibody and a scFv derived from a murine anti-diDTPA can be produced. A flexible linker, such as GGGS connects the scFv to the constant region of the heavy chain of the anti-CEA antibody. Alternatively, the scFv can be connected to the constant region of the light chain of hMN-14. Appropriate linker sequences necessary for the in-frame connection of the heavy chain Fd to the scFv are introduced into the VL and VK domains through PCR reactions. The DNA fragment encoding the scFv is then ligated into a staging vector containing a DNA sequence encoding the CH1 domain. The resulting scFv-CH1 construct is excised and ligated into a vector containing a DNA sequence encoding the VH region of an anti-CEA antibody. The resulting vector can be used to transfect mammalian cells for the expression of the bi-specific fusion protein.

Large quantities of bscAb and fusion proteins can be produced using *Escherichia coli* expression systems. See, e.g., Zhenping et al., *Biotechnology*, 14: 192–196, 1996. A functional bscAb can be produced by the coexpression in *E. coli* of two "cross-over" scFv fragments in which the $V_L$ and $V_H$ domains for the two fragments are present on different polypeptide chains. The V light-chain ($V_L$) and V heavy-chain ($V_H$) domains of two antibodies of interest are isolated using standard PCR methods. The cDNA's are then ligated into a bacterial expression vector such that C-terminus of the $V_L$ domain of the first antibody of interest is ligated via a linker to the N-terminus of the $V_H$ domain of the second antibody. Similarly, the C-terminus of the $V_L$ domain of the second antibody of interest is ligated via a linker to the N-terminus of the $V_H$ domain of the first antibody. The resulting dicistronic operon is placed under transcriptional control of a strong promoter, e.g., the *E. coli* alkaline phosphatase promoter which is inducible by phosphate starvation. Alternatively, single-chain fusion constructs have successfully been expressed in *E. coli* using the lac promoter and a medium consisting of 2% glycine and 1% Triton X-100. See, e.g., Yang et al., *Appl. Environ. Microbiol.*, 64: 2869–2874, 1998. An *E. coli*, heat-stable, enterotoxin II signal sequence is used to direct the peptides to the periplasmic space. After secretion, the two peptide chains associate to form a non-covalent heterodimer which possesses both antigen binding specificities. The bscAb is purified using standard procedures known in the art, e.g., Staphylococcal protein A chromatography.

Functional bscAb and fusion proteins also can be produced in the milk of transgenic livestock. See, e.g., Colman, A., *Biochem. Soc. Symp.*, 63: 141–147, 1998; U.S. Pat. No. 5,827,690. The bscAb fragment, obtained as described above, is cloned into an expression vector containing a promoter sequence that is preferentially expressed in mammary epithelial cells. Examples include, but are not limited to, promoters from rabbit, cow and sheep casein genes, the cow α-lactoglobulin gene, the sheep β-lactoglobulin gene and the mouse whey acid protein gene. Preferably, the inserted bscAb is flanked on its 3' side by cognate genomic sequences from a mammary-specific gene. This provides a polyadenylation site and transcript-stabilizing sequences. The expression cassette is then injected into the pronuclei of fertilized, mammalian eggs, which are then implanted into the uterus of a recipient female and allowed to gestate. After birth, the progeny are screened for the presence of the introduced DNA by Southern analysis. Milk from transgenic females is analyzed for the presence and functionality of the bscAb using standard immunological methods known in the art. The bscAb can be purified from the milk using standard methods known in the art. Transgenic production of bscAb in milk provides an efficient method for obtaining large quantities of bscAb.

Functional bscAb and fusion proteins also can be produced in transgenic plants. See, e.g., Fiedler et al., *Biotech.*, 13: 1090–1093, 1995; Fiedler et al., *Immunotechnology*, 3: 205–216, 1997. Such production offers several advantages including low cost, large scale output and stable, long term storage. The bscAb fragment, obtained as described above, is cloned into an expression vector containing a promoter sequence and encoding a signal peptide sequence, to direct the protein to the endoplasmic recticulum. A variety of promoters can be utilized, allowing the practitioner to direct the expression product to particular locations within the plant. For example, ubiquitous expression in tobacco plants can be achieved by using the strong cauliflower mosaic virus 35S promoter, while organ specific expression is achieved via the seed specific legumin B4 promoter. The expression cassette is transformed according to standard methods known in the art. Transformation is verified by Southern analysis. Transgenic plants are analyzed for the presence and functionality of the bscAb using standard immunological methods known in the art. The bscAb can be purified from the plant tissues using standard methods known in the art.

Additionally, transgenic plants facilitate long term storage of bscAb and fusion proteins. Functionally active scFv proteins have been extracted from tobacco leaves after a week of storage at room temperature. Similarly, transgenic tobacco seeds stored for 1 year at room temperature show no loss of scFv protein or its antigen binding activity.

Functional bscAb and fusion proteins also can be produced in insect cells. See, e.g., Mahiouz et al., *J. Immunol. Methods*, 212: 149–160 (1998). Insect-based expression systems provide a means of producing large quantities of homogenous and properly folded bscAb. The baculovirus is a widely used expression vector for insect cells and has been successfully applied to recombinant antibody molecules. See, e.g., Miller, L. K., *Ann. Rev. Microbiol.*, 42: 177 (1988); Bei et al., *J. Immunol. Methods*, 186: 245 (1995). Alternatively, an inducible expression system can be utilized by generating a stable insect cell line containing the bscAb construct under the transcriptional control of an inducible promoter. See, e.g., Mahiouz et al., *J. Immunol. Methods*, 212: 149–160 (1998). The bscAb fragment, obtained as described above, is cloned into an expression vector containing the *Drosphila* metallothionein promoter and the human HLA-A2 leader sequence. The construct is then transfected into *D. melanogaster* SC-2 cells. Expression is induced by exposing the cells to elevated amounts of copper, zinc or cadmium. The presence and functionality of the bscAb is determined using standard immunological methods known in the art. Purified bscAb is obtained using standard methods known in the art.

The presence of hydrophilic chelate moieties on the targetable conjugate helps to ensure rapid in vivo clearance. In addition to hydrophilicity, chelates are chosen for their metal-binding properties, and are changed at will since, at least for those targetable conjugates whose bsAb epitope is part of the peptide or is a non-chelated hapten, recognition of the metal-chelate complex is no longer an issue. Particularly useful metal-chelate combinations include 2-benzyl-DTPA and its monomethyl and cyclohexyl analogs, used with scandium-47, iron-52, cobalt-55, gallium-67, gallium-68, indium-111, zirconium-89, yttrium-90, terbium-161, lutetium-177, bismuth-212, bismuth-213, and actinium-225 for radio-imaging and RAIT. The same chelators, when complexed with non-radioactive metals, such as manganese, iron and gadolinium can be used for MRI, when used along with the bsAbs of the invention. Macrocyclic chelators such as NOTA, DOTA, and TETA are of use with a variety of metals and radiometals, most particularly with radionuclides of gallium, yttrium and copper, respectively. DTPA and DOTA-type chelators, where the ligand includes hard base chelating functions such as carboxylate or amine groups, are most effective for chelating hard acid cations, especially Group IIa and Group IIIa metal cations. Such metal-chelate complexes can be made very stable by tailoring the ring size to the metal of interest. Other ring-type chelators such as macrocyclic polyethers, which are of interest for stably binding nuclides such as radium-223 for RAIT are encompassed by the invention. Porphyrin chelators may be used with numerous radiometals, and are also useful as certain non-radioactive metal complexes for bsAb-directed immuno-phototherapy. More than one type of chelator may be conjugated to a carrier to bind multiple metal ions, e.g., non-radioactive ions, diagnostic radionuclides and/or therapeutic radionuclides. One example is a bis-$^{111}$In-DTPA conjugate that also bears a DOTA-$^{90}$Y chelate.

Chelators such as those disclosed in U.S. Pat. No. 5,753,206, especially thiosemicarbazonylglyoxylcysteine(TscG-Cys) and thiosemicarbazinyl-acetylcysteine (TscA-Cys) chelators are advantageously used to bind soft acid cations of Tc, Re, Bi and other transition metals, lanthanides and actinides that are tightly bound to soft base ligands, especially sulfur- or phosphorus-containing ligands. It can be useful to link more than one type of chelator to a peptide, e.g., a DTPA or similar chelator for, say In(III) cations, and a thiol-containing chelator, e.g., TscG-Cys, for Tc cations. Because antibodies to a di-DTPA hapten are known (Barbet '395, supra) and are readily coupled to a targeting antibody to form a bsAb, it is possible to use a peptide hapten with non-radioactive diDTPA chelates and another chelate for binding a radioisotope, in a pretargeting protocol, for targeting the radioisotope. One example of such a peptide is Ac-Lys(DTPA)-TyrLys(DTPA)-Lys(TscG-Cys-)-NH$_2$ (SEQ ID NO: 3). This peptide can be preloaded with In(III) and then labeled with 99-m-Tc cations, the In(III) ions being preferentially chelated by the DTPA and the Tc cations binding preferentially to the thiol-containing TscG-CysC. Other hard acid chelators such as NOTA, DOTA, TETA and the like can be substituted for the DTPA groups, and Mabs specific to them can be produced using analogous techniques to those used to generate the anti-di-DTPA Mab.

It will be appreciated that two different hard acid or soft acid chelators can be incorporated into the targetable conjugate, e.g., with different chelate ring sizes, to bind preferentially to two different hard acid or soft acid cations, due to the differing sizes of the cations, the geometries of the chelate rings and the preferred complex ion structures of the cations. This will permit two different metals, one or both of which may be radioactive or useful for MRI enhancement, to be incorporated into a targetable conjugate for eventual capture by a pre-targeted bsAb.

Chelators are coupled to the carrier portion of a targetable conjugate using standard chemistries. For instance, excess 2-(p-isothiocyanato)benzyl-DTPA is reacted with peptide NH$_2$ groups to form thiourea bonds between the p-isothiocyanate of the chelator and the free 1-α and 6-ε-amino groups of the peptide, when a peptide is the targetable conjugate. Alternatively, the bis-anhydride of DTPA can be coupled directly to a free amine group on the peptide. The desired chelator-peptide is purified chromatographically and is ready for use as a metal binding agent. Similarly, DOTA is mono-activated at one carboxyl group using a carbodiimide, and two DOTA units are coupled to the peptide's free amino-groups. Chelators bearing groups specifically reactive with thiols are used for reaction with peptides such as Ac-Cys-D-Tyr-D-Trp-Gly-D-Cys-Gly-D-Tyr-D-Trp-NH$_2$. Such a chelator is exemplified by 2-(p-bromoacetamido) benzyl-DTPA, which may be used to alkylate the peptide's free thiol groups under mild, neutral conditions.

Chelator-peptide conjugates may be stored for long periods as solids. They may be metered into unit doses for metal-binding reactions, and stored as unit doses either as solids, aqueous or semi-aqueous solutions, frozen solutions or lyophilized preparations. They may be labeled by well-known procedures. Typically, a hard acid cation is introduced as a solution of a convenient salt, and is taken up by the hard acid chelator and possibly by the soft acid chelator. However, later addition of soft acid cations leads to binding thereof by the soft acid chelator, displacing any hard acid cations which may be chelated therein. For example, even in the presence of an excess of non-radioactive 111-InCl$_3$, labeling with 99m-Tc(V) glucoheptonate or with Tc cations generated in situ with stannous chloride and Na99m-TcO$_4$ proceeds quantitatively on the soft acid chelator. Other soft acid cations such as Re-186, Re-188, Bi-213 and divalent or trivalent cations of Mn, Co, Ni, Pb, Cu, Cd, Au, Fe, Ag (monovalent), Zn and Hg, especially Cu-64 and Cu-67, and the like, some of which are useful for radioimmunodiagnosis or radioimmunotherapy, can be loaded onto the carrier peptide by analogous methods. Re cations also can be generated in situ from perrhenate and stannous ions or a prereduced rhenium glucoheptonate or other transchelator can be used. Because reduction of perrhenate requires more stannous ion (typically above 200 ug/mL final concentration) than is needed for the reduction of technetium, extra care needs to be taken to ensure that the higher levels of stannous ion do not reduce sensitive disulfide bonds such as those present in disulfide-cyclized peptides. A convenient way to prepare ReO metal complexes of the TscG-Cys-ligands is by reacting the peptide with ReOCl$_3$(P(Ph$_3$))$_2$ but it is also possible to use other reduced species such as ReO(ethylenediamine)$_2$.

In one embodiment of the present invention, the bsAb is given at some time prior to administration of the therapeutic agent which is associated with the targetable conjugate. The doses and timing of the reagents can be readily worked out by a skilled artisan, and are dependent on the specific nature of the reagents employed. If a bsAb-F(ab')$_2$ derivative is given first, then a waiting time of 1–6 days before administration of the targetable conjugate would be appropriate. If an IgG-Fab' bsAb conjugate is the primary targeting vector, then a longer waiting period before administration of the targetable conjugate would be indicated, probably in the range of 3–15 days. If a bi-specific fusion protein, for example an anti-CEA Fab×anti-peptide scFv, is the primary targeting vector, a shorter waiting period before administration of the targetable conjugate would be indicated, probably in the range of 1–5 days.

In another embodiment, the present invention can be used in Boron Neutron Capture Therapy (BNCT) protocols. BNCT is a binary system designed to deliver ionizing radiation to tumor cells by neutron irradiation of tumor-localized boron-10 atoms. BNCT is based on the nuclear reaction which occurs when a stable isotope, isotopically enriched B-10 (present in 19.8% natural abundance), is irradiated with thermal neutrons to produce an alpha particle and a Li-7 nucleus. These particles have a path length of about one cell diameter, resulting in high linear energy transfer. Just a few of the short-range 1.7 MeV alpha particles produced in this nuclear reaction are sufficient to target the cell nucleus and destroy it. Success with BNCT of cancer requires methods for localizing a high concentration of boron-10 at tumor sites, while leaving non-target organs essentially boron-free. Compositions and methods for treating tumors in patients using pre-targeting bsAb for BNCT are described in U.S. Pat. No. 6,228,362 and can easily be modified in accordance with the present invention. Additionally, other elements are suitable for neutron capture reactions. One example is uranium. Uranium, in large amounts, can be bound by naturally occurring chelating agents such as ferritin. Such strategies have been described in U.S. Pat. No. 6,228,362, are easily adaptable to the present invention and are hereby incorporated in their entirety by reference.

In another embodiment of the practice of the invention, the bsAb is administered prior to administration of a diagnostic agent which is associated with the targetable conjugate. After sufficient time has passed for the bsAb to target to the diseased tissue, the diagnostic agent is administered. Subsequent to administration of the diagnostic agent, imaging can be performed. Tumors can be detected in body cavities by means of directly or indirectly viewing various structures to which light is delivered and then collected. Lesions at any body site can be viewed so long as nonionizing radiation can be delivered and recaptured from these structures. For example, positron emission tomography (PET) which is a high resolution, non-invasive, imaging technique can be used with the inventive antibodies for the visualization of human disease. In PET, 511 keV gamma photons produced during positron annihilation decay are detected. Similar pre-targeting strategies for PET using Fluorine-18 and Gallium-68 have been described, respectively in U.S. Pat. No. 6,187,284. The methodologies described in these applications are easily adaptable to the present invention and are hereby incorporated in their entirety by reference.

As another example, the present inventive antibodies or antibody fragments can be used in a method of photodynamic diagnosis or therapy. In a diagnostic method, a diagnostic agent is injected, for example, systemically, and laser-induced fluorescence can be used by endoscopes to detect sites of cancer which have accreted the light-activated agent. For example, this has been applied to fluorescence bronchoscopic disclosure of early lung tumors (Doiron et al., *Chest* 76:32, 1979, incorporated herein by reference; and references cited above). In another example, the inventive antibodies and antibody fragments can be used in single photon emission. For example, a Tc-99m-labeled diagnostic agent can be administered to a patient following administration of the inventive antibodies or antibody fragments. The patient is then scanned with a gamma camera which produces single-photon emission computed tomographic images and defines the lesion or tumor site.

The present invention also can be used in a method for photodynamic therapy. In this methodology, a photosensitizer, for example a hematoporphyrin derivative such as dihematoporphyrin ether, is administered to a patient. Anti-tumor activity is initiated by the use of strong red light, for example, at 630 nanometers wavelength. Alternate photo-sensitizers can be utilized, including those useful at longer wavelengths, where skin is less photosensitized by the sun. Examples of such photosensitizers include, but are not limited to, benzoporphyrin monoacid ring A (BPD-MA), tin etiopurpurin (SnET2), sulfonated aluminum phthalocyanine (AlSPc) and lutetium texaphyrin (Lutex).

Certain cytotoxic drugs that are useful for anticancer therapy are relatively insoluble in serum. Some are also quite toxic in an unconjugated form, and their toxicity is considerably reduced by conversion to prodrugs. Conversion of a poorly soluble drug to a more soluble conjugate, e.g., a glucuronide, an ester of a hydrophilic acid or an amide of a hydrophilic amine, will improve its solubility in the aqueous phase of serum and its ability to pass through venous, arterial or capillary cell walls and to reach the interstitial fluid bathing the tumor. Cleavage of the prodrug deposits the less soluble drug at the target site. Many examples of such prodrug-to-drug conversions are disclosed in U.S. Pat. Nos. 5,851,527 and 6,071,490.

In an alternative embodiment, the enzyme-carrier conjugate can be mixed with the targeting bsAb prior to administration to the patient. After a sufficient time has passed for the enzyme-carrier-bsAb conjugate to localize to the target site and for unbound conjugate to clear from circulation, a prodrug is administered. As discussed above, the prodrug is then converted to the drug in situ by the pre-targeted enzyme.

Certain cytotoxic drugs that are useful for anticancer therapy are relatively insoluble in serum. Some are also quite toxic in an unconjugated form, and their toxicity is considerably reduced by conversion to prodrugs. Conversion of a poorly soluble drug to a more soluble conjugate, e.g., a glucuronide, an ester of a hydrophilic acid or an amide of a hydrophilic amine, will improve its solubility in the aqueous phase of serum and its ability to pass through venous, arterial or capillary cell walls and to reach the interstitial fluid bathing the tumor. Cleavage of the prodrug deposits the less soluble drug at the target site. Many examples of such prodrug-to-drug conversions are disclosed in Hansen U.S. Ser. No. 08/445,110.

Conversion of certain toxic substances such as aromatic or alicyclic alcohols, thiols, phenols and amines to glucuronides in the liver is the body's method of detoxifying them and making them more easily excreted in the urine. One type of anti-tumor drug that can be converted to such a substrate is epirubicin, a 4-epimer of doxorubicin (Adriamycin), which is an anthracycline glycoside and has been shown to be a substrate for human beta-D-glucuronidase See, e.g., Arcamone, *Cancer Res.*, 45:5995, 1985. Other analogues with fewer polar groups are expected to be more lipophilic and show greater promise for such an approach. Other drugs or toxins with aromatic or alicyclic alcohol, thiol or amine groups are candidates for such conjugate formation. These drugs, or other prodrug forms thereof, are suitable candidates for the site-specific enhancement methods of the present invention.

The prodrug CPT-11 (irinotecan) is converted in vivo by carboxylesterase to the active metabolite SN-38. SN-38 is a highly effective anti-tumor agent; however, therapeutic doses can not be administered to patients due to its toxicity. One application of the invention, therefore, is to target such therapies to the tumor site using a bsAb specific for a tumor-associated antigen and a hapten (e.g. di-DTPA) followed by injection of a di-DTPA-carboxylesterase conjugate. Once a suitable tumor-to-background localization ratio has been achieved, the CPT-11 is given and the tumor-localized carboxylesterase serves to convert CPT-11 to SN-38 at the tumor. Due to its poor solubility, the active SN-38 will remain in the vicinity of the tumor and, consequently, will exert an effect on adjacent tumor cells that are negative for the antigen being targeted. This is a further advantage of the method. Modified forms of carboxy-lesterases have been described and are within the scope of the invention. See, e.g., Potter et al., *Cancer Res.*, 58:2646–2651 and 3627–3632, 1998.

Etoposide is a widely used cancer drug that is detoxified to a major extent by formation of its glucuronide and is within the scope of the invention. See, e.g., Hande et al., *Cancer Res.*, 48: 1829–1834, 1988. Glucuronide conjugates can be prepared from cytotoxic drugs and can be injected as therapeutics for tumors pre-targeted with mAb-glucuronidase conjugates. See, e.g., Wang et al., *Cancer Res.*, 52:4484–4491, 1992. Accordingly, such conjugates also can be used with the pre-targeting approach described here. Similarly, designed prodrugs based on derivatives of daunomycin and doxorubicin have been described for use with carboxylesterases and glucuronidases. See, e.g., Bakina et al., *J. Med. Chem.*, 40:4013–4018, 1997. Other examples of prodrug/enzyme pairs that can be used within the present invention include, but are not limited to, glucuronide prodrugs of hydroxy derivatives of phenol mustards and beta-glucuronidase; phenol mustards or CPT-1 and carboxypeptidase; methotrexate-substituted alpha-amino acids and carboxypeptidase A; penicillin or cephalosporin conjugates of drugs such as 6-mercaptopurine and doxorubicin and beta-lactamase; etoposide phosphate and alkaline phosphatase.

In other embodiments of the present invention, the enzyme capable of activating a prodrug at the target site or improving the efficacy of a normal therapeutic by controlling the body's detoxification pathways is conjugated to the hapten. The enzyme-hapten conjugate is administered to the patient following administration of the pre-targeting bsAb and is directed to the target site. After the enzyme is localized at the target site, a cytotoxic drug is injected, which is known to act at the target site, or a prodrug form thereof which is converted to the drug in situ by the pre-targeted enzyme. As discussed above, the drug is one which is detoxified to form an intermediate of lower toxicity, most commonly a glucuronide, using the mammal's ordinary detoxification processes. The detoxified intermediate, e.g., the glucuronide, is reconverted to its more toxic form by the pre-targeted enzyme and thus has enhanced cytotoxicity at the target site. This results in a recycling of the drug. Similarly, an administered prodrug can be converted to an active drug through normal biological processes. The pre-targeted enzyme improves the efficacy of the treatment by recycling the detoxified drug. This approach can be adopted for use with any enzyme-drug pair. In an alternative embodiment, the enzyme-hapten conjugate can be mixed with the targeting bsAb prior to administration to the patient. After a sufficient time has passed for the enzyme-hapten-bsAb conjugate to localize to the target site and for unbound conjugate to clear from circulation, a prodrug is administered. As discussed above, the prodrug is then converted to the drug in situ by the pre-targeted enzyme.

In another embodiment of the present invention, the carrier portion of the targetable conjugate is conjugated to a prodrug. The pre-targeting bsAb is administered to the patient and allowed to localize to the target and substantially clear circulation. At an appropriate later time, a targetable conjugate comprising a prodrug, for example poly-glutamic acid (SN-38-ester)$_{10}$, is given, thereby localizing the prodrug specifically at the tumor target. It is known that tumors have increased amounts of enzymes released from intracellular sources due to the high rate of lysis of cells within and around tumors. A practitioner can capitalize on this fact by appropriately selecting prodrugs capable of being activated by these enzymes. For example, carboxylesterase activates the prodrug poly-glutamic acid (SN-38-ester)$_{10}$ by cleaving the ester bond of the poly-glutamic acid (SN-38-ester)$_{10}$ releasing large concentrations of free SN-38 at the tumor. Alternatively, the appropriate enzyme also can be targeted to the tumor site.

After cleavage from the targetable conjugate, the drug is internalized by the tumor cells. Alternatively, the drug can be internalized as part of an intact complex by virtue of cross-linking at the target. The targetable conjugate can induce internalization of tumor-bound bsAb and thereby improve the efficacy of the treatment by causing higher levels of the drug to be internalized.

A variety of carriers are well-suited for conjugation to prodrugs, including polyamino acids, such as polylysine, polyglutamic (E) and aspartic acids (D), including D-amino acid analogs of the same, co-polymers, such as poly(Lys-Glu) {poly[KE]}, advantageously from 1:10 to 10:1. Copolymers based on amino acid mixtures such as poly(Lys-Ala-Glu-Tyr) (SEQ ID NO: 4) (KAEY; 5:6:2:1) can also be employed. Smaller polymeric carriers of defined molecular weight can be produced by solid-phase peptide synthesis techniques, readily producing polypeptides of from 2–50 residues in chain length. A second advantage of this type of reagent, other than precise structural definition, is the ability to place single or any desired number of chemical handles at certain points in the chain. These can be used later for attachment of recognition and therapeutic haptens at chosen levels of each moiety.

Poly(ethylene) glycol [PEG] has desirable in vivo properties for a bi-specific antibody prodrug approach. Ester linkages between the hydroxyl group of SN-38 and both ends of a standard di-hydroxyl PEG can be introduced by insertion of diacids such as succinic acid between the SN-38 and PEG hydroxyl groups, to generate species such as SN-38-O—CO(CH2)$_2$CO—O-PEG-O—CO(CH2)$_2$CO—OSN-38. The di-SN-38-PEG produced can be considered as the shortest member of the class of SN-38-polymer prodrugs. The desirable in vivo properties of PEG derivatives and the limited loading capacity due to their dimeric functionality led to the preparation of PEG co-polymers having greater hapten-bearing capacity such as those described by Poiani et al. See, e.g., Poiani et al. *Bioconjugate Chem.*, 5:621–630, 1994. PEG derivatives are activated at both ends as their bis(succinimidyl)carbonate derivatives and co-polymerized with multi-functional diamines such as lysine. The product of such co-polymerization, containing (-Lys(COOH)—PEG-Lys(COOH)—PEG-)$_n$ repeat units wherein the lysyl carboxyl group is not involved in the polymerization process, can be used for attachment of SN-38 residues. The SN-38 residues are reacted with the free carboxyl groups to produce SN-38 esters of the (-Lys-(COOH)—PEG-Lys(COOH)—PEG-)$_n$ chain.

Other synthetic polymers that can be used to carry recognition haptens and prodrugs include N-(2-hydroxypropyl) methacrylamide (HMPA) copolymers, poly(styrene-co-maleic acid/anhydride (SMA), poly(divinylether maleic anhydride) (DIVEMA), polyethylene-imine, ethoxylated polyethylene-imine, starburst dendrimers and poly(N-vinylpyrrolidone) (PVP). As an example, DIVEMA polymer comprised of multiple anhydride units is reacted with a limited amount of SN-38 to produce a desired substitution ratio of drug on the polymer backbone. Remaining anhydride groups are opened under aqueous conditions to produce free carboxylate groups. A limited number of the free carboxylate groups are activated using standard water-soluble peptide coupling agents, e.g. 1-ethyl-3-(3-dimethylaminopropyl)carbodiimide hydrochloride (EDC), and coupled to a recognition moiety bearing a free amino group. An example of the latter is histamine, to which antibodies have been raised in the past.

A variety of prodrugs can be conjugated to the carrier portion of the targetable conjugate. The above exemplifications of polymer use are concerned with SN-38, the active metabolite of the prodrug CPT-11 (irinotecan). SN-38 has an aromatic hydroxyl group that was used in the above descriptions to produce aryl esters susceptible to esterase-type enzymes. Similarly the camptothecin analog topotecan, widely used in chemotherapy, has an available aromatic hydroxyl residue that can be used in a similar manner as described for SN-38, producing esterase-susceptible polymer-prodrugs.

Doxorubicin also contains aromatic hydroxyl groups that can be coupled to carboxylate-containing polymeric carriers using acid-catalyzed reactions similar to those described for the camptothecin family. Similarly, doxorubicin analogs like daunomycin, epirubicin and idarubicin can be coupled in the same manner. Doxorubicin and other drugs with amino 'chemical handles' active enough for chemical coupling to polymeric carriers can be effectively coupled to carrier molecules via these free amino groups in a number of ways. Polymers bearing free carboxylate groups can be activated in situ (EDC) and the activated polymers mixed with doxorubicin to directly attach the drug to the side-chains of the polymer via amide bonds. Amino-containing drugs can also be coupled to amino-pendant polymers by mixing commercially available and cleavable cross-linking agents, such as ethylene glycobis(succinimidylsuccinate) (EGS, Pierce Chemical Co., Rockford, Ill.) or bis-[2-(succinimido-oxycarbonyloxy)ethyl]sulfone (BSOCOES, Molecular Biosciences, Huntsville, Ala.), to cross-link the two amines as two amides after reaction with the bis(succinimidyl) ester groups. This is advantageous as these groups remain susceptible to enzymatic cleavage. For example, (doxorubicin-EGS)$_n$-poly-lysine remains susceptible to enzymatic cleavage of the diester groups in the EGS linking chain by enzymes such as esterases. Doxorubicin also can be conjugated to a variety of peptides, for example, HyBnK(DTPA) YK(DTPA)-NH$_2$, using established procedures (HyBn=p-H$_2$NNHC$_6$H$_4$CO$_2$H). See Kaneko et al., *J. Bioconjugate Chem.*, 2: 133–141, 1991.

In one preferred embodiment, the therapeutic conjugate comprises doxorubicin coupled to a carrier comprising amine residues and a chelating agent, such as DTPA, to form a DTPA-peptide-doxorubicin conjugate, wherein the DTPA forms the recognition moiety for a pretargeted bsMAb. Preferably, the carrier comprises a tyrosyl-lysine dipeptide, e.g., Tyr-Lys(DTPA)-NH$_2$, and more preferably still it comprises Lys(DTPA)-Tyr-Lys(DTPA)-NH$_2$ Doxorubicin phenyl hydrazone conjugates to bis-DPTA containing peptides are particularly desirable in a therapeutic context.

Methotrexate also has an available amino group for coupling to activated carboxylate-containing polymers, in a similar manner to that described for doxorubicin. It also has two glutamyl carboxyl groups (alpha and gamma) that can be activated for coupling to amino-group containing polymers. The free carboxylate groups of methotrexate can be activated in situ (EDC) and the activated drug mixed with an amino-containing polymer to directly attach the drug to the side-chains of the polymer via amide bonds. Excess unreacted or cross-reacted drug is separated readily from the polymer-drug conjugate using size-exclusion or ion-exchange chromatography.

Maytansinoids and calicheamicins (such as esperamycin) contain mixed di- and tri-sulfide bonds that can be cleaved to generate species with a single thiol useful for chemical manipulation. The thiomaytensinoid or thioesperamycin is first reacted with a cross-linking agent such as a maleimidopeptide that is susceptible to cleavage by peptidases. The C-terminus of the peptide is then activated and coupled to an amino-containing polymer such as polylysine.

In still other embodiments, the bi-specific antibody-directed delivery of therapeutics or prodrug polymers to in vivo targets can be combined with bi-specific antibody delivery of radionuclides, such that combination chemotherapy and radioimmunotherapy is achieved. Each therapy can be conjugated to the targetable conjugate and administered simultaneously, or the nuclide can be given as part of a first targetable conjugate and the drug given in a later step as part of a second targetable conjugate. In one simple embodiment, a peptide containing a single prodrug and a single nuclide is constructed. For example, the tripeptide Ac-Glu-Gly-Lys-NH$_2$ can be used as a carrier portion of a targetable conjugate, whereby SN-38 is attached to the gamma glutamyl carboxyl group as an aryl ester, while the chelate DOTA is attached to the epsilon amino group as an amide, to produce the complex Ac-Glu(SN-38)-Gly-Lys (DOTA)-NH$_2$. The DOTA chelate can then be radiolabeled with various metals for imaging and therapy purposes including In-111, Y-90, Sm-153, Lu-177 and Zr-89. As the metal-DOTA complex may represent the recognizable hapten on the targetable conjugate, the only requirement for the metal used as part of the DOTA complex is that the secondary recognition antibody also used recognizes that particular metal-DOTA complex at a sufficiently high affinity. Generally, this affinity (log $K_a$) is between 6–11. Polymeric peptides such as poly[Glu(SN-38)$_{10}$-Lys(Y-90-DOTA)$_2$] can be given as readily as the more chemically defined lower MW reagent above, and are indeed preferred. Also, triply substituted polymers can be used, such as poly[Glu(Sn-38)$_{10}$-Lys(Y-90-DOTA)$_n$(histamine-succinate)$_m$, where n and m are integers, such that the recognition agent is independent of the radioimmunotherapy agent. The prodrug is activated by carboxylesterases present at the tumor site or by carboxylesterases targeted to the site using a second targetable conjugate.

Alternatively, a combination therapy can be achieved by administering the chemotherapy and radioimmunotherapy agents in separate steps. For example, a patient expressing CEA-tumors is first administered bsAb with at least one arm which specifically binds CEA and at least one other arm which specifically binds the targetable conjugate whose hapten is a conjugate of yttrium-DOTA. Later the patient is treated with a targetable conjugate comprising a conjugate of yttrium-DOTA-beta-glucuronidase. After sufficient time for bsAb and enzyme localization and clearance, a second targetable conjugate, comprising Ac-Glu(SN-38)-Gly-Lys (Y-90-DOTA)-NH$_2$, is given. The second targetable conjugate localizes to the tumor by virtue of bsAb at the tumor that are not already bound to a first targetable conjugate. First targetable conjugates which are localized to the target site act on the Ac-Glu(SN-38)-Gly-Lys(Y-90-DOTA)-NH$_2$ to liberate the free SN-38 drug. Localization of both the prodrug and its respective enzyme to the target site enhances the production of active drug by ensuring that the enzyme is not substrate limited. This embodiment constitutes a marked improvement of current prodrug methodologies currently practiced in the art.

Another advantage of administering the prodrug-polymer in a later step, after the nuclide has been delivered as part of a previously given targetable conjugate, is that the synergistic effects of radiation and drug therapy can be manipulated and, therefore, maximized. It is hypothesized that tumors become more 'leaky' after RAIT due to radiation damage. This can allow a polymer-prodrug to enter a tumor more completely and deeply. This results in improved chemotherapy.

Alternatively, the RAIT therapy agent can be attached to bsAb rather the targetable conjugate. For example, an anti-CEAxanti-DTPA bsAb conjugated to Y-90-DOTA is administered first to a patient with CEA-expressing tumors. In this instance, advantage is taken of the selectivity of certain anti-chelate mabs in that an anti-indium-DTPA antibody do not bind to a yttrium-DOTA chelate. After the Y-90-DOTA-anti-CEA×anti-indium-DTPA has maximized at the tumor and substantially cleared non-target tissue, a conjugate of indium-DTPA-glucuronidase is injected and localized specifically to the CEA tumor sites. The patient is then injected with a polymer-prodrug such as poly(Glu)(SN-38)$_{10}$. The latter is cleaved selectively at the tumor to active monomeric SN-38, successfully combining chemotherapy with the previously administered RAIT.

It should also be noted that a bi-specific antibody or antibody fragment can be used in the present method, with at least one binding site specific to an antigen at a target site and at least one other binding site specific to an enzyme. Such an antibody can bind the enzyme prior to injection, thereby obviating the need to covalently conjugate the enzyme to the antibody, or it can be injected and localized at the target site and, after non-targeted antibody has substantially cleared from the circulatory system of the mammal, enzyme can be injected in an amount and by a route which enables a sufficient amount of the enzyme to reach the pre-targeted bsAb and bind to it to form an antibody-enzyme conjugate in situ.

In one embodiment of the invention, a clearing agent may be used which is given between doses of the bsAb and the targetable conjugate. The present inventors have discovered that a clearing agent of novel mechanistic action may be used with the invention, namely a glycosylated anti-idiotypic Fab' fragment targeted against the disease targeting arm(s) of the bsAb. In this embodiment an anti-CEA (MN 14 Ab)×anti-peptide bsAb is given and allowed to accrete in disease targets to its maximum extent. To clear residual bsAb, an anti-idiotypic Ab to MN-14, termed WI2, is given as a glycosylated Fab' fragment. The clearing agent binds to the bsAb in a monovalent manner, while its appended glycosyl residues direct the entire complex to the liver, where rapid metabolism takes place. Then the therapeutic which is associated with the targetable conjugate is given to the patient. The WI2 Ab to the MN-14 arm of the bsAb has a high affinity and the clearance mechanism differs from other disclosed mechanisms (see Goodwin, et al., ibid), as it does not involve cross-linking, because the WI2-Fab' is a monovalent moiety.

In accordance with yet another aspect of the present invention, the present invention provides a kit suitable for treating or identifying diseased tissues in a patient, comprising a bi-specific antibody or antibody fragment having at least one arm that specifically binds a targeted tissue and at least one other arm that specifically binds a targetable conjugate, a first targetable conjugate which comprises a carrier portion which comprises or bears at least one epitope recognizable by the at least one other arm of the bi-specific antibody or antibody fragment, and one or more conjugated therapeutic or diagnostic agents, or enzymes, and, optionally, a clearing composition useful for clearing non-localized antibodies and antibody fragments. When the first targetable conjugate comprises an enzyme, the kit may optionally contain a prodrug, when the enzyme is capable of converting the prodrug to a drug at the target site, a drug which is capable of being detoxified in the patient to form an intermediate of lower toxicity, when the enzyme is capable of reconverting the detoxified intermediate to a toxic form, and, therefore, of increasing the toxicity of the drug at the target site, or a prodrug which is activated in the patient through natural processes and is subject to detoxification by conversion to an intermediate of lower toxicity, when the enzyme is capable of reconverting the detoxified intermediate to a toxic form, and, therefore, of increasing the toxicity of the drug at the target site, or a second targetable conjugate which comprises a carrier portion which comprises or bears at least one epitope recognizable by the at least one other arm of the bi-specific antibody or antibody fragment, and a prodrug, when the enzyme is capable of converting the prodrug to a drug at the target site. Instruments which facilitate identifying or treating diseased tissue also can be included in the kit. Examples include, but are not limited to application devices, such as syringes. Solutions required for utilizing the disclosed invention for identifying or treating diseased tissue also can be included in the kit.

EXAMPLES

Example 1

Synthesis of a Peptide Antigen

The peptide, Ac-Phe-Lys(Ac)-Tyr-Lys(Ac)-OH (SEQ ID NO: 1), is assembled using a resin for solid-phase synthesis and attaching the first residue (lysine) to the resin as the differentially protected derivative alpha-Fmoc-Lys(Aloc)-OH. The alpha-Fmoc protecting group is selectively removed and the Fmoc-Tyr(OBut), alpha-Fmoc-Lys(Aloc)-OH, and Fmoc-Phe-OH added with alternate cycles of coupling and alpha-amino group deprotection. The Aloc- and OBut-side-chain protecting groups are then removed by reaction with TFA and the free alpha- and epsilon-amino groups are capped by reaction with acetic anhydride to give Ac-Phe-Lys(Ac)-Tyr-Lys(Ac)-OH (SEQ ID NO: 1).

Example 2

Coupling of Ac-Phe-Lys(Ac)-Tyr-Lys(Ac)-OH SEQ ID NO: 1) to KLH

The peptide, Ac-Phe-Lys(Ac)-Tyr-Lys(Ac)-OH (SEQ ID NO: 1), dissolved in water and pH-adjusted to 4.0 with 1N HCl, is treated with a molar equivalent of 1-ethyl-3(3-dimethylaminopropyl) carbodiimide and allowed to react for 1 h at 4° C. Keyhold limpet hemocyanin (KLH) buffered at pH 8.5 is treated with a 100-fold molar excess of the activated peptide and the conjugation reaction is allowed to proceed for 1 h at 4° C. The peptide-KLH conjugate is purified from unreacted peptide by size-exclusion chromatography and used for antibody production.

Example 3

Generation of an Anti-Peptide Ab

Immunocompetent mice are injected with a mixture of the peptide antigen in complete Freund's adjuvant. Two booster shots of the peptide mixed with incomplete Freund's adjuvant are administered over the next several weeks. Spleen cells are harvested from the animals and fused with Sp2/0-Ag14 myeloma cells. Culture supernatants of the resulting clones are analyzed for anti-peptide reactivity by ELISA, using plates coated with the original peptide immunogen. Enzyme-deficient hybridomas are isolated to enable selection of fused cell lines, and selected clones grown in culture media to produce the anti-peptide Abs.

Example 4

Purification of Anti-Peptide Ab

Anti-peptide Ab is purified chromatographically using a protein A column to isolate the IgG fraction, followed by ion-exchange columns to clean the desired product. The Ab of interest is finally purified by using an affinity column comprised of the peptide of interest bound to a solid support, prepared by chemically coupling said peptide to activated beads or resin.

Example 5

Digestion of Anti-Peptide Ab to F(ab')$_2$

The anti-peptide Ab is incubated with 200 µg/µL of pepsin at pH 4 for one hour and purified by a tandem column of protein A, to remove undigested IgG, followed by G-50-Sephadex, to remove low molecular weight contaminants.

Example 6

Reduction of Anti-Peptide-Ab to Fab'-SH

The anti-peptide-F(ab')$_2$ is reduced to a Fab' fragment by reaction with a freshly prepared cysteine solution in 0.1M PBS, containing 10 mM EDTA. The progress of the reaction is followed by HPLC, and when complete, in about 1 h, the Fab'-SH is purified by spin-column chromatography and stored in deoxygenated buffer at pH<5 containing 10 mM EDTA.

Example 7

Oxidative Coupling of Anti-CEA-IgG to a Maleimide Moiety

Anti-CEA Ab IgG is oxidized by reaction with 10 mM sodium periodate for 90 minutes at 4° C., in the dark. The oxidized Ab is purified by spin-column chromatography and mixed with an excess of the cross-linker 4-(4-maleimidophenyl) butyric acid hydrazide (MPBH). The reaction is allowed to proceed for 2 h and the IgG-hydrazone-meleimide purified by spin-column chromatography. The hydrazone bond is reduced by reaction with 10 mM sodium cyanoborohydride and repurified.

Example 8

Preparation of Anti-CEA-IgG×Anti-Peptide-Fab' Bi-Specific Ab

The IgG-hydrazide-maleimide from Example 7) is treated with an equimolar amount of anti-peptide Fab'-SH, prepared in Example 6, at pH 6.0, for 30 minutes at room temperature. Remaining free thiol groups are blocked by a 30-minute reaction with iodoacetamide. The bi-specific Ab anti-CEA-IgG×anti-peptide-Fab' is purified by size-exclusion chromatography to remove unreacted Fab', followed by affinity chromatography using solid-phase-bound peptide to separate IgG×Fab' from unreacted IgG.

Example 9

Synthesis of Ac-Phe-Lys(Bz-DTPA)-Tyr-Lys(Bz-DTPA)-NH$_2$ (SEQ ID NO: 1)

The peptide, Ac-Phe-Lys(DTPA)-Tyr-Lys(DTPA)-NH$_2$ (SEQ ID NO: 1), is assembled using a resin for solid-phase synthesis and attaching the first residue (lysine to said resin as the differentially protected derivative alpha-Fmoc-Lys (Aloc)-OH. The alpha-Fmoc protecting group is selectively removed and the Fmoc-Tyr(OBut), alpha-Fmoc-Lys(Aloc)-OH, and Fmoc-Phe-OH added with alternate cycles of coupling and alpha-amino group deprotection. The Aloc-side-chain is removed by reaction with palladium (0) catalyst. Alternatively, Boc-group protecting groups may be used which may be removed by reaction with TFA and the free amino groups reacted with excess of the ITC-Bz-DTPA. After removing excess Bz-DTPA, the alpha-amino group is capped by reaction with acetic anhydride, and the entire peptide removed from the resin with TFA (with concomitant deprotection of the tyrosyl residue) to give Ac-Phe-Lys(Bz-DTPA)-Tyr-Lys(Bz-DTPA)-NH$_2$ (SEQ ID NO: 1).

Example 10

Radiolabeling of Ac-Phe-Lys(Bz-DTPA)-Tyr-Lys(Bz-DTPA)-NH$_2$ (SEQ ID NO: 1) with Y-90

The title peptide in 100-fold molar excess is mixed with yttrium-90 radionuclide in acetate buffer at pH 5.5. The radiolabeling is complete and quantitative after 30 minutes.

Example 11

Conjugation of a Carboxylesterase to Di-DTPA-Peptide

Carboxylesterase (5 mg) in 0.2 M phosphate buffer, pH 8.0, is treated with a five-fold molar excess of the cross-linking agent sulfo-succinimidyl-[4-maleimidomethyl]-cyclohexane-1-carboxylate (sulfo-SMCC). After stirring two hours at room temperature, the activated enzyme is separated from low molecular weight contaminants using a spin-column of G-25 Sephadex and equilibrated in 0.1 M phosphate buffer, pH 7, containing 1 mM EDTA. The tetrapeptide N-acetyl-Cys.Lys(DTPA).Tyr.Lys(DTPA).NH$_2$ (SEQ ID NO: 5) (ten-fold molar excess) is added to the activated enzyme and dissolved in the same buffer as used in the spin-column. After stirring for one hour at room temperature, the carboxylesterase-Cys.Lys(DTPA).Tyr.Lys (DTPA).NH$_2$ (SEQ ID NO: 5) peptide conjugate is purified from unreacted peptide by spin-column chromatography on G-25 Sephadex in 0.25 M acetate buffer, pH 6.0. Successful conjugation is demonstrated by indium-111 labeling of an aliquot of the conjugate, and analysis by size-exclusion HPLC.

Example 12

Use of anti-CEA-IgG×anti-Peptide-Fab' Bi-specific Ab for RAIT

A patient with a CEA-expressing tumor burden is given anti-CEA-IgG×anti-peptide-Fab' bi-specific Ab. Seven days later, the patient is given Y-90-di-Bz-DTPA-peptide (from Example 10). The Y-90-labeled peptide clears rapidly from non-target tissue but localizes avidly to sites pre-targeted with the anti-CEA-IgG×anti-peptide-Fab' bi-specific Ab, effecting destruction of tumors.

Example 13

Preparation of a Galactose-WI2-Fab' Clearing Agent

The anti-idiotypic Ab to MN-14, termed WI2 is digested to a F(ab')$_2$ fragment using pepsin, as outlined in Example 4. The F(ab')$_2$ is reduced to a Fab' fragment using a low molecular weight thiol, as outlined in Example 6. At the end of the reduction, the Fab'-SH is purified by spin-column chromatography and reacted with excess iodoacetamide to block hinge-region thiol groups and prevent reassociation. After repurification from excess iodoacetamide the Fab' is reacted with a 400-fold molar excess of the galactosylation agent, the thio-imidate of cyanomethyl-2,3,4,6-tetra-O-acetyl-1-thio-beta-D-galactopyranoside (see Karacay et al.). The galactosylated protein is purified by two spin-columns and the galactose:Fab' radio determined by MALDI-MS.

Example 14

Use of Anti-CEA-IgG×Anti-Peptide Fab' Bi-Specific Ab for RAIT, with a bsAb Clearing Step A patient with a CEA-expressing tumor burden is given anti-CEA-IgG (MN-14)×anti-peptide-Fab' bi-specific Ab. Three days later, the patient is given a clearing dose of galactose-WI2-Fab'. Twenty-four hours after the clearing dose of a galactose-WI2-Fab', the patient is given Y-90-di-Bz-DTPA-peptide. The Y-90-labeled peptide clears rapidly from non-target tissue but localizes avidly to sites pretargeted with the anti-CEA-IgG×anti-peptide-Fab' bi-specific Ab, effecting destruction of tumors.

Example 15

Synthesis of Ac-Lys(DTPA)-TyrLys(DTPA)-Lys (TscG-Cys-)-NH$_2$ (SEQ ID NO: 3) (IMP 192)

The first amino acid, Aloc-Lys(Fmoc)-OH was attached to 0.21 mmol Rink amide resin on the peptide synthesizer followed by the addition of the Tc-99m ligand binding residues Fmoc-Cys(Trt)-OH and TscG to the side chain of the lysine using standard Fmoc automated synthesis protocols to form the following peptide: Aloc-Lys(TscG-Cys(Trt)-rink resin. The Aloc group was then removed by treatment of the resin with 8 mL of a solution containing 100 mg Pd[P(Ph)3]4 dissolved in 10 mL CH$_2$Cl$_2$, 0.75 mL glacial acetic acid and 2.5 ml diisopropylethyl amine. The resin mixture was then treated with 0.8 ml tributyltin hydride and vortex mixed for 60 min. The peptide synthesis was then continued on the synthesizer to make the following peptide: Lys(Aloc)-Tyr-Lys(Aloc)-Lys(TscG-Cys-)(SEQ ID NO: 3)-rink resin. The N-terminus was acetylated by vortex mixing the resin for 60 mm with 8 mL of a solution containing 10 mL DMF, 3 mL acetic anhydride, and 6 mL diisopropylethylamine. The side chain Aloc protecting groups were then removed as described above and the resin treated with piperidine using the standard Fmoc deprotection protocol to remove any acetic acid which may have remained on the resin. Activated DTPA and DTPA Addition: The DTPA, 5 g was dissolved in 40 mL 1.0 M tetrabutylammonium hydroxide in methanol. The methanol was removed under hi-vacuum to obtain a viscous oil. The oil was dissolved in 50 mL DMF and the volatile solvents were removed under hi-vacuum on the rotary evaporator. The DMF treatment was repeated two more times. The viscous oil was then dissolved in 50 ml DMF and mixed with 5 g HBTU. An 8 ml aliquot of the activated DTPA solution was then added to the resin which was vortex mixed for 14 hr. The DTPA treatment was repeated until the resin gave a negative test for amines using the Kaiser test. Cleavage and Purification: The peptide was then cleaved from the resin by treatment with 8 ml of a solution made from 30 ml TFA, 1 ml triisopropylsilane, and 1 ml ethanedithiol for 60 mm. The crude cleaved peptide was precipitated by pouring into 30 ml ether and was collected by centrifugation. The peptide was then purified by reverse phase HPLC using a 4×30 cm Waters preparative C-18 Delta-Pak column (15 μm, 100 Å). The HPLC fractions were collected and lyophilized to obtain a fraction which contained the desired product by ESMS (MH±1590). Kit Formulation: The peptide was formulated into lyophilized kits which contained 78 μg of the peptide, 0.92 mg non-radioactive InCl$_3$, 100 μg stannous chloride, 3 mg gentisic acid, and HPCD (10% on reconstitution).

Example 16

Tc-99m Labeling and Stability

An IMP 192 kit was labeled by reconstituting the contents of the vial with 1.5 mL of saline which contained 25 mCi Na$^{99m}$TcO$_4$. The kit was incubated at room temperature for 10 mm and then heated in a boiling water bath for 15 mm. The labeled peptide solution was then cooled to room temperature. Aliquots were removed for stability studies. The aliquots were diluted 1:10 in saline, 1 mM cysteine in 0.05M phosphate pH 7.5, and fresh human serum. The original kit solution, the saline dilution, and the cysteine challenge were incubated at room temperature while the serum sample was incubated at 37° C. The samples were monitored by HPLC and ITLC. The labeled peptide was stable in the in vitro tests. The retention time of the labeled peptide in serum was shifted from 6.3 mm to 7.3 min. The shift may be due to ion pairing of some serum component with the peptide.

| Sample | Initial Label | First Time Point | Second Time Point | ITLC 24 hr Saturated NaCl |
|---|---|---|---|---|
| Kit Room Temp. | 1% Void Vol 99% Peptide (6.4 mm) | 3 hr 1% Void Vol 99% Peptide | 21 hr 5% Void Vol 95% Peptide | 5% Solvent Front 94% Origin |
| Saline Dilution Room Temp. | | 1.5 hr 1% Void Vol 99% Peptide | 19 hr 4% Void Vol 96% Peptide | 2.3% Solvent Front 97% Origin |
| Cys Challenge 1 mM in 0.05 M | | 1 hr 2% Void Vol | 19.5 hr 11% Void Vol | 7.4% Solvent Front |

-continued

| Sample | Initial Label | First Time Point | Second Time Point | ITLC 24 hr Saturated NaCl |
|---|---|---|---|---|
| phosphate pH 7.5 Room Temp. | | 98% Peptide | 89% Peptide | 91.3% Origin |
| Human Serum 37° C. | | 2 hr 1% Void Vol 7% 6 min 92% 7.2 min | 20 hr 3% Void Vol 15% 6 min 82% 7.3 min | 1.7% Solvent Front 96% Origin |

Example 17

Preparation of hMN-14×734 (Fab×Fab)

This bsMAb was prepared by crosslinking the hMN-14 Fab'$_{SH}$ (a humanized monoclonal anti-CEA antibody) and 734 Fab'$_{mal}$ (a murine anti-diDTPA) fragments, analogously to Example 8. The Fab'$_{SH}$ fragments of hMN-14 and 734 were prepared by reduction of the F(ab')$_2$ fragments with 10 mM 2-mercaptoethylamine in the presence of 10 mM EDTA at pH 7.3 for 60 min at 37° C. Fab'$_{SH}$ was collected after spin column (Penefsky) purification (Sephadex G-50–80, 50 mM NaOAc, 0.5 mM EDTA, pH 5.3) Maleimide group(s) were introduced onto 734 Fab'$_{SH}$ fragment using 4 mM N,N'-o-phenylenedimaleimide at RT for 60 min. Spin column purification was used to isolate the Fab'$_{mal}$. Crosslinking of 734 Fab'$_{mal}$ and hMN-14 Fab'$_{SH}$ was allowed to proceed 16 h at 4° C. at 1:1 molar ratio. To break the disulfide bonds which might have formed during this time, the reaction mixture was treated with 10 mM 2-mercaptoethylamine for 1 h at pH 5.3 at 23° C. The SH groups were blocked with N-ethylmaleimide at pH 6.4. The reaction mixture was applied to a spin column to remove excess small molecular weight compounds. The bsAb was then isolated after purification on an analytical size exclusion HPLC column, Bio-Sil SEC-250. The HPLC retention time of the purified bsAb was 10.23 min.

Example 18

HPLC Binding Studies

The bsMAb was radioiodinated using chloramine T (Greenwood and Hunter). Binding of the radioiodinated bsMAbs to CEA, WI2 (rat anti-MN-14 idiotypic antibody) and radiolabeled peptidyl DTPA chelate was examined on analytical size exclusion HPLC. Approximately 90% of the radioiodinated bsMAb bound to CEA upon treatment with 10–20× molar excess of CEA. The bsMAb complexed with radiolabeled indium-DTPA chelates (IMP-156 or IMP-192).

IMP 156 Ac-Phe-Lys(DTPA)-Tyr-Lys(DTPA)-NH$_2$

Example 19

Serum Stability

Radioiodinated bsMAb was tested for stability in fresh human serum at 37° C. under a humidified 5% CO$_2$ atmosphere. Aliquots were examined on SE-HPLC. In order to detect radioiodine associated with serum proteins, the aliquots were mixed with WI2 to shift the bsMAb peak to earlier retention times. The bsMAbs showed 3–5% loss of binding capacity to WI2 after 48 h incubation in serum. Slight aggregate formation (4–7%) was observed upon incubation of the bsMAbs in serum for 72 h.

Example 20

99m-Tc-IMP-192

In vitro stability of the Tc-99m complex of this peptidyl chelate was established by incubations in saline, fresh human serum and 10 mM cysteine for up to 20 h. In vivo stability was examined by analysis of urine collected from a mouse injected with 99m-Tc-IMP-192 in a pretargeting experiment. The activity excreted in the urine appears to be the intact peptide because the activity still binds to the antibody as shown by SE-HPLC. Biodistribution studies of 99m-Tc-IMP-192 in normal BALB/c mice showed rapid blood clearance, Table 1. The in vitro and in vivo studies clearly demonstrate stability of 99m-Tc-IMP-192.

TABLE 1

Clearance of 99m-Tc-IMP-192 in BALB/c mice.

| Tissue | % ID/g | | | |
|---|---|---|---|---|
| | 1 h | 2 h | 4 h | 24 h |
| Liver | 0.27 ± 0.18 | 0.22 ± 0.16 | 0.09 ± 0.02 | 0.04 ± 0.0 |
| Spleen | 0.08 ± 0.01 | 0.09 ± 0.3 | 0.05 ± 0.02 | 0.03 ± 0.01 |
| Kidney | 4.16 ± 0.75 | 4.05 ± 0.60 | 3.21 ± 0.99 | 1.21 ± 0.08 |
| Lungs | 0.50 ± 0.23 | 0.29 ± 0.08 | 0.19 ± 0.04 | 0.05 ± 0.00 |
| Blood | 0.30 ± 0.09 | 0.21 ± 0.03 | 0.14 ± 0.04 | 0.05 ± 0.01 |
| Stomach | 0.39 ± 0.18 | 0.42 ± 0.18 | 0.27 ± 0.33 | 0.02 ± 0.01 |
| Small int | 1.37 ± 0.75 | 0.60 ± 0.06 | 0.21 ± 0.09 | 0.03 ± 0.01 |
| Lg. Int. | 0.41 ± 0.54 | 1.53 ± 0.45 | 1.58 ± 0.70 | 0.15 ± 0.14 |
| Muscle | 0.10 ± 0.06 | 0.05 ± 0.00 | 0.03 ± 0.01 | 0.00 ± 0.0 |
| Urine | 169 ± 95 | 57 ± 15 | 6.30 ± 4.53 | 0.20 ± 0.02 |

Example 21

Construction and Expression of hMN14Fab-734scFv

Recombinant methods were used to produce a monovalent bi-specific fusion protein comprising a Fab fragment derived from a humanized monoclonal anti-CEA antibody and a scFv derived from a murine anti-diDTPA. See FIG. 3. The structure of single chain 734 (734scFv) was designed as GGGS-VL (SEQ ID NO: 6)-(GGGGS)3-VH (SEQ ID NO: 7), in which the proximal GGGS (SEQ ID NO: 6) provides a flexible linkage for the scFv to be connected to the constant region of the heavy chain of hMN-14 (FIG. 1). Alternatively, the scFv can be connected to the constant region of the light chain of hMN-14. Appropriate linker sequences necessary for the in-frame connection of the hMN14 heavy chain Fd to 734scFv were introduced into the VL and VK domains of 734 by PCR reactions using specific primer sets. PCR-amplification of 734VL was performed using the primer set 734VLscFv5'(Cys) and 734VLscFv3' (respectively, SEQ ID NO's: 1 & 2). The primer 734VLscFv5'(Cys) represents the sense-strand sequence encoding the first four residues (PKSC (SEQ ID NO: 8)) of the human IgG1 hinge, linked in-frame to the first six residues (QLVVTQ (SEQ ID NO: 9)) of 734 VL, via a short flexible linker, GGGS (SEQ ID NO: 6). One cysteine of the human hinge was included because it is required for the interchain disulfide linkage between the hMN14 heavy chain Fd-734scFv fusion and the hMN14 light chain. A Pst1 site was incorporated (underline) to facilitate ligation at the intronic sequence connecting the CH1 domain and the hinge. The primer 734VLscFv3' represents the anti-sense sequence encoding the last six residues (TKLKIL (SEQ ID NO: 10)) of the 734 $V_L$ domain and a portion of the flexible linker sequence (GGGGSGGGG (SEQ ID NO: 11)), which is fused in-frame downstream of the $V_L$ domain. Following PCR amplification, the amplified product (~400 bp) first was treated with T4 DNA polymerase to remove the extra "A" residue added to the termini during PCR-amplification and subsequently was digested with Pst1. The resultant product was a double-stranded DNA fragment with a Pst1 overhang and a blunt end. PCR amplification of 734VH was performed using the primer set 734VHscFv5' and 734VHscFV3' (Sac1). Primer 734VHscFv5' (SEQ ID NO: 3) represents the sense-strand sequence encoding the remaining part of the flexible linker sequence (SGGGGS (SEQ ID NO: 12)) connecting the VL and VH sequences, and the first six residues (EVKLQE (SEQ ID NO: 13)) of the 734 VH domain. Primer 734VHscFv3'(Sac1) (SEQ ID NO: 4) represents the anti-sense sequence encoding the last six residues (TVTVSS (SEQ ID NO: 14)) of 734 VH. Also included is a translation stop codon (*). The restriction sites Eag1 (bold) and Sac1 (underlined) were incorporated downstream of the stop codon to facilitate subcloning. Similarly, the PCR-amplified $V_H$ product of ~400 bp was first treated with T4 DNA polymerase to remove the extra "A" residues at the PCR product termini, and then digested with Sac1, resulting in a $V_H$ DNA fragment with a blunt end-sticky end configuration. A pBlueScript (Stratagene, La Jolla)-based staging vector (HC1kbpSK) containing a SacII fragment of the human IgG1 genomic sequence was constructed. The genomic SacII fragment contains a partial 5' intron, the human IgG1 CH1 domain, the intronic sequence connecting the CH1 to the hinge, the hinge sequence, the intronic sequence connecting the hinge to the CH2 domain, and part of the CH2 domain. The segment containing the hinge and part of the CH2 domain in HC1kbpSK was removed by Pst1/Sac1 digestion, and the cloning site generated was used to co-ligate the $V_L$ (Pst1/blunt) and $V_H$ (blunt/Sac1) PCR products prepared above. The CH1 domain in the resultant construct (CH1–734pSK) is connected to the 734scFv gene sequence via an intron (FIG. 4). Since the genomic SacII fragment for IgG1 only included part of the 5' intron sequence flanking the CH1 domain, the full intronic sequence was restored by inserting the remaining intronic sequence as a BamH1/SacII segment, into the corresponding sites of the CH1–734pSK. The BamH1/Eag1 fragment containing the full 5' intron, CH1 domain, connecting intron, 5 hinge-residues, short GGGS linker, and a 734scFv sequences was then isolated, and used to replace the HindIII/Eag1 segment containing the human genomic IgG1 constant sequence in the hMN14pdHL2 vector. A HNB linker (SEQ ID NO: 5) with a BamH1 overhang on one end and a HindIII overhang on the other was used to facilitate the BamH1/Eag1 fragment ligation into the HindIII/Eag1 site in the hMN14pdHL2 vector. The resultant vector was designated hMN14–734pdHL2 and can be used to transfect mammalian cells for the expression of the bispecific protein. The hMN14pdHL2 vector was derived from the vector, pdHL2, which has previously been described. See Losman et al., Cancer Supplement, 80:2660, 1997. Construction of hMN14pdHL2 was performed by replacing the VH and VK domains of hLL2pdHL2 with that of hMN14 using standard molecular biology techniques (FIG. 5). The hMN14–734pdHL2 vector was transfected into SP2/0 cells by electroporation and the cell clones secreting bsAb were identified. The bsAb purified from cell culture supernatant (clone 341.1G6) on a protein L column (Pierce, Rockford, Ill.) is a 75 kD protein (based on amino acid sequence calculation) that co-migrated with the 66 kD marker in non-reducing SDS-PAGE probably due to secondary structure (FIG. 2, lane 2). Under reducing conditions, bands corresponding to a heavy (50 kD) and a light (25 kD) chain were observed (FIG. 2, lane 4). Kappa chain monomers (25 kD) and dimers (50 kD) secreted by the transfectoma also were co-purified (FIG. 2, lane 2) since protein L binds to kappa light chains of human, mouse and rat. Further separation of bsAb from kappa mono- and dimers is accomplished with ion-exchange chromatography. Purified hMN14Fab-734scFv shows specific binding to both CEA and In-DTPA-BSA in a dose dependent manner.

Example 22

Transgenic Production of bscAb in Milk

A bscAb fragment is cloned into an expression vector containing a 5' casein promoter sequence and 3' untranslated genomic sequences that flank the insertion site. The expression cassette is then injected into the pronuclei of fertilized, mouse eggs, using procedures standard in the art. The eggs are then implanted into the uterus of a recipient female and allowed to gestate. After birth, the progeny are screened for the presence of the introduced DNA by Southern analysis. Milk from transgenic females is analyzed for the presence and functionality of the bscAb using standard immunological methods known in the art. The bscAb can be purified from the milk by complementary binding to an immobilized antigen, column chromotography or other methods known in the art.

Example 23

Transgenic Production of bscAb in Plants

A bscAb fragment is cloned into an expression vector containing a shortened legumin B4 promoter plus 54 base pairs of LeB4 untranslated RNA leader from *Vicia faba* and encoding a LeB4 signal peptide, to direct the protein to the endoplasmic recticulum. The expression cassette is transformed into tobacco leaf discs according to the methods described by Zambryski et al., using *Agrobacterium*-mediated gene transfer. Transformation is verified by Southern analysis. Transgenic plants are analyzed for the presence and functionality of the bscAb using standard immunological methods known in the art. The bscAb can be purified from the plant tissues using standard methods known in the art.

Example 24

Pretargeting Experiments

Female nude mice (Taconic NCRNU, 3–4 weeks old) with GW 39 tumor xenografts were used for the pretargeting experiments. Tumors were 0.3–0.8 g.

TABLE 2

Biodistribution of 125-I-hMN-14 × 734 bsAb and 111-In-indium-IMP-156 peptide in nude mice bearing GW-39 tumor xenografts: hMN-14 × 734 was allowed 48 h for localization prior to 111-In-indium-IMP-156 injection. Biodistribution was performed 3 h post 111-In-indium-IMP-156. bsAb:peptide ratio administered, 1:0.03. Five animals per time point.

|  | 125-I-hMN-14 × 734 | | 111-In-indium-IMP-156 | |
| --- | --- | --- | --- | --- |
| Tissue | % ID/g | T/NT | % ID/g | T/NT |
| tumor | 2.9 ± 1.1 | 1 | 5.2 ± 1.9 | 1 |
| Liver | 0.1 ± 0.06 | 19 ± 6 | 0.5 ± 0.09 | 10.6 ± 3.5 |
| Spleen | 0.5 ± 0.03 | 6.3 ± 1.2 | 0.5 ± 0.1 | 12 ± 6 |
| Kidney | 0.3 ± 0.08 | 9.3 ± 1.8 | 1.9 ± 0.5 | 2.6 ± 0.5 |
| Lungs | 0.3 ± 0.1 | 12 ± 3 | 0.4 ± 0.1 | 12 ± 2 |
| Blood | 0.3 ± 0.1 | 11 ± 2 | 0.7 ± 0.2 | 7.6 ± 1.5 |

TABLE 3

Control group showing the clearance of 111-In-indium-IMP-156 at 3 h after injection.

|  | % ID/g | T/NT |
| --- | --- | --- |
| Tumor | 0.14 ± 0.02 | 1 |
| Liver | 0.42 ± 0.1 | 0.3 ± 0.1 |
| Spleen | 0.28 ± 0.09 | 0.5 ± 0.1 |
| Kidney | 0.93 ± 0.13 | 0.2 ± 0.03 |
| Lungs | 0.04 ± 0.01 | 3.5 ± 0.7 |
| Blood | 0.05 ± 0.01 | 3.1 ± 0.7 |

TABLE 4

Nude mice bearing GW 39 tumor xenografts were administered 125-I-labeled bsAb (5 µCi, 15 µg, $1.5 \times 10^{-10}$ mol). hMN-14 × 734 was allowed 24 h for localization and clearance before administering 99m-Tc-IMP-192 (10 µCi, $1.6 \times 10^{-11}$ mol of peptide). Biodistribution studies were performed at 30 min, 1, 3 and 24 h post 99m-Tc-IMP-192 injection, five animals per time point. BsAb:peptide, 1:0.1.

| | % ID/g | | | |
| --- | --- | --- | --- | --- |
| Tissue | 30 min | 1 h | 3 h | 24 h |
| 125-I-hMN-14 × 734 | | | | |
| Tumor | 4.9 ± 1.1 | 6.0 ± 2.3 | 5.5 ± 1.1 | 3.3 ± 0.7 |
| Liver | 0.6 ± 0.1 | 0.5 ± 0.2 | 0.5 ± 0.1 | 0.1 ± 0.02 |
| Spleen | 0.8 ± 0.3 | 0.7 ± 0.3 | 0.7 ± 0.2 | 0.2 ± 0.03 |
| Kidney | 0.5 ± 0.1 | 0.5 ± 0.1 | 0.5 ± 0.1 | 0.1 ± 0.02 |
| Lungs | 0.9 ± 0.3 | 0.8 ± 0.2 | 0.8 ± 0.3 | 0.3 ± 0.1 |
| Blood | 0.9 ± 0.3 | 1.2 ± 0.4 | 1.1 ± 0.3 | 0.2 ± 0.07 |
| 99m-Tc-LMP-192 | | | | |
| Tumor | 11.4 ± 4.8 | 14.3 ± 3.6 | 12.6 ± 5.2 | 8.7 ± 3.3 |
| Liver | 1.4 ± 0.3 | 0.9 ± 0.2 | 0.6 ± 0.1 | 0.4 ± 0.08 |
| Spleen | 1.2 ± 0.4 | 0.8 ± 0.2 | 0.5 ± 0.1 | 0.4 ± 0.2 |
| Kidney | 9.9 ± 6.1 | 4.6 ± 0.7 | 2.4 ± 0.5 | 1.2 ± 0.3 |
| Lungs | 4.2 ± 3.4 | 3.6 ± 1.9 | 1.0 ± 0.3 | 0.3 ± 0.1 |
| Blood | 4.3 ± 1.2 | 3.5 ± 0.9 | 1.7 ± 0.4 | 0.6 ± 0.2 |

TABLE 5

Nude mice bearing GW 39 tumor xenografts were administered 125-I-labeled bsAb (5 µCi, 15 µg, $1.5 \times 10^{-10}$ mol). hMN-14 × 734 was allowed 24 h for localization and clearance before administering 99m-Tc-IMP-192 (10 µCi, $1.6 \times 10^{-11}$ mol of peptide). Biodistribution studies were performed at 30 min, 1, 3 and 24 h post 99m-Tc-IMP-192 injection, five animals per time point. BsAb:peptide, 1:0.1.

| | Tumor/non-tumor ratio | | | |
| --- | --- | --- | --- | --- |
| Tissue | 30 min | 1 h | 3 h | 24 h |
| 125-I-hMN-14 × | | | | |
| Liver | 8.8 ± 1.5 | 12.1 ± 5.5 | 10.3 ± 2.5 | 23.8 ± 3.5 |
| Spleen | 6.4 ± 1.6 | 9.3 ± 4.0 | 7.9 ± 1.7 | 18.2 ± 4.0 |
| Kidney | 10.0 ± 2.6 | 12.5 ± 4.5 | 11.1 ± 3.0 | 27.3 ± 4.6 |
| Lungs | 6.2 ± 2.3 | 8.4 ± 4.6 | 7.2 ± 2.3 | 12.4 ± 6.6 |
| Blood | 5.7 ± 2.1 | 4.9 ± 1.2 | 5.1 ± 1.3 | 14.5 ± 3.6 |
| 99m-Tc-IMP-192 | | | | |
| Liver | 7.9 ± 1.7 | 15.7 ± 5.4 | 20.7 ± 7.6 | 22.3 ± 7.4 |
| Spleen | 9.4 ± 1.0 | 19.5 ± 8.6 | 22.9 ± 7.5 | 23.8 ± 3.5 |
| Kidney | 1.2 ± 0.2 | 3.1 ± 0.6 | 5.2 ± 1.5 | 7.3 ± 1.9 |
| Lungs | 3.7 ± 1.7 | 5.5 ± 3.6 | 13.5 ± 7.1 | 30.8 ± 14.4 |
| Blood | 2.7 ± 0.7 | 4.2 ± 1.3 | 7.3 ± 2.3 | 16.1 ± 6.4 |

TABLE 6

Control group of nude mice bearing GW-39 tumors received 99m-Tc-IMP-192 (10 µCi, $1.6 \times 10^{-11}$ mol of peptide) and were sacrificed 3 h later.
99m-Tc-IMP-192

| Tissue | % ID/g |
| --- | --- |
| Tumor | 0.2 ± 0.05 |
| Liver | 0.3 ± 0.07 |
| Spleen | 0.1 ± 0.05 |
| Kidney | 2.6 ± 0.9 |
| Lungs | 0.2 ± 0.07 |
| Blood | 0.2 ± 0.09 |

The percentage of the available DTPA binding sites on the tumor bound bsAb filled with 99m-Tc-IMP-192 was calculated from the above data assuming one peptide bound to one bsAb molecule. However, it is possible that one peptide molecule can crosslink two molecules of bsAb.

TABLE 7

Percentage of the available DTPA binding sites on the tumor bound bsAb filled with 99m-Tc-IMP-192

| time | % saturation on hMN-14 × 734 |
| --- | --- |
| 30 min | 25.4 |
| 1 h | 25.8 |
| 3 h | 25 |
| 24 h | 28 |

The foregoing experimental data show that: the humanized×murine bsAb retained its binding capability to CEA and indium-DTPA; the hMN-14×734 (Fab×Fab) effectively targets a tumor; the dual functional peptidyl Tc-99m chelator was stable; 99m-Tc-IMP-192 complexed to tumor-localized hMN-14×734 and was retained for at least 24 h; and imaging of tumors is possible at early time points (1–3 h) post 99m-Tc-IMP-192 injection.

Example 25

Use of Anti-CEA Fab×Anti-Peptide scFv Fusion Protein for RAIT, with a bsAb Clearing Step A patient with a CEA-expressing tumor burden is given an anti-CEA Fab×anti-peptide scFv fusion protein. Three days later, the patient is given a clearing dose of galactose-W12-Fab'. Twenty-four hours after the clearing dose of a galactose-W12-Fab', the patient is given Y-90-di-Bz-DTPA-peptide. The Y-90-labeled peptide clears rapidly from non-target tissue but localizes avidly to sites pretargeted with the anti-CEA Fab×anti-peptide scFv fusion protein, effecting destruction of tumors.

Example 26

Use of Anti-CEA-IgG×Anti-Peptide Fab' Bi-Specific Ab for Prodrug Therapy with a bsAb Clearing Step A patient with colorectal cancer is given an injection of an IgG-hMN-14×anti-peptide Fab' bsAb. After 48 h, to allow for maximum accretion in tumors, the patient is given a clearing dose of galactose-WI2-Fab'. This amount is between 5 and 15 times the amount of primary bsAb remaining in circulation at the time-point specified. Three hours after administration of the galactose-W12-Fab', a tumor-saturating amount of the carboxylesterase-Cys.Lys(DTPA).Tyr.Lys(DTPA).NH$_2$ (SEQ ID NO: 5) conjugate from example 11 is given, and allowed to clear circulation and normal tissues. After an additional three hours, a standard chemotherapy dose of CPT-11 is administered to the patient. This protocol effectively generates free SN-38 specifically at the tumor target sites and effects the destruction of tumor cells.

Example 27

Preparation of a Carboxylesterase-DTPA Conjugate

Two vials of rabbit liver carboxylesterase (SIGMA; protein content ~17 mg) are reconstituted in 2.2 ml of 0.1 M sodium phosphate buffer, pH 7.7 and mixed with a 25-fold molar excess of CA-DTPA using a freshly prepared stock solution (~25 mg/ml) of the latter in DMSO. The final concentration of DMSO in the conjugation mixture is 3% (v/v). After 1 hour of incubation, the mixture is pre-purified on two 5-mL spin-columns (Sephadex G50/80 in 0.1 M sodium phosphate pH 7.3) to remove excess reagent and DMSO. The eluate is purified on a TSK 3000G Supelco column using 0.2 M sodium phosphate pH 6.8 at 4 ml/min. The fraction containing conjugate is concentrated on a Centricon-10™ concentrator, and buffer-exchanged with 0.1 M sodium acetate pH 6.5. Recovery: 0.9 ml, 4.11 mg/ml (3.7 mg). Analytical HPLC analysis using standard conditions, with in-line UV detection, revealed a major peak with a retention time of 9.3 min and a minor peak at 10.8 min in 95-to-5 ratio. Enzymatic analysis showed 115 enzyme units/mg protein, comparable to unmodified carboxylesterase. Mass spectral analyses (MALDI mode) of both unmodified and DTPA-modified CE shows an average DTPA substitution ratio near 1.5. A metal-binding assay using a known excess of indium spiked with radioactive indium confirmed the DTPA:enzyme ratio to be 1.24 and 1.41 in duplicate experiments. Carboxylesterase-DTPA is labeled with In-111 acetate at a specific activity of 12.0 mCi/mg, then treated with excess of non-radioactive indium acetate, and finally treated with 10 mM EDTA to scavenge off excess non-radioactive indium. Incorporation by HPLC and ITLC analyses is 97.7%. A HPLC sample is completely complexed with a 20-fold molar excess of bispecific antibody hMN-14 Fab'×734 Fab', and the resultant product further complexes with W12 (anti-ID to hMN-14), with the latter in 80-fold molar excess with respect to bispecific antibody.

Example 28

Synthesis of IMP 224

An amount of 0.0596 g of the phenyl hydrazine containing peptide IMP 221 ($H_2N$—NH—$C_6H_4$—CO-Lys(DTPA)-Tyr-Lys(DTPA)-$NH_2$ $MH^+$ 1322, made by Fmoc SPPS) was mixed with 0.0245 g of Doxorubicin hydrochloride in 3 mL of DMF. The reaction solution was allowed to react at room temperature in the dark. After 4 hours an additional 0.0263 g of IMP 221 was added and the reaction continued overnight. The entire reaction mixture was then purified by HPLC on a Waters Nova-Pak (3–40×100 mm segments, 6 µm, 60 Å) prep column eluting with a gradient of 80:20 to 60:40 Buffer A:B over 40 min (Buffer A=0.3% $NH_4OAc$, Buffer B=0.3% $NH_4OAc$ in 90% $CH_3CN$). The fractions containing product were combined and lyophilized to afford 0.0453 g of the desired product, which was confirmed by ESMS $MH^+$1847.

Example 29

IMP 224 Kit Formulation

The peptide of Example 28 was formulated into kits for In-111 labeling. A solution was prepared which contained 5.014 g 2-hydroxypropyl-β-cyclodextrin, and 0.598 g citric acid in 85 mL. The solution was adjusted to pH 4.20 by the addition of 1 M NaOH and diluted with water to 100 mL. An amount of 0.0010 g of the peptide IMP 224 was dissolved in 100 mL of the buffer, and 1 mL aliquots were sterile filtered through a 0.22 µm Millex GV filter into 2 mL lyophilization vials which were immediately frozen and lyophilized.

Example 30

In-111 Labeling of IMP 224 Kits

The In-111 was dissolved in 0.5 mL water and injected into the lyophilized kit. The kit solution was incubated at room temperature for 10 min then 0.5 mL of a pH 7.2 buffer which contained 0.5 M NaOAc and 2.56×10$^{-5}$ M cold indium was added.

Example 31

In-Vitro Stability of IMP 224 Kits

An IMP 224 kit was labeled as described with 2.52 mCi of In-111. Aliquots (0.15 mL, 370 µCi) were withdrawn and mixed with 0.9 mL 0.5 M citrate buffer pH 4.0, 0.9 mL 0.5 M citrate buffer pH 5.0, and 0.9 mL 0.5 M phosphate buffer pH 7.5. The stability of the labeled peptide was followed by reverse phase HPLC. HPLC Conditions: Waters Radial-Pak C-18 Nova-Pak 8×100 mm, Flow Rate 3 mL/min, Gradient: 100% A=0.3% $NH_4OAc$ to 100% B=90% $CH_3CN$, 0.3% $NH_4OAc$ over 10 min.

TABLE 8

In-Vitro Stability of In/In-111 IMP 224

| Kit | | 4.0 pH | | 5.0 pH | | 7.5 pH | |
| --- | --- | --- | --- | --- | --- | --- | --- |
| ime | Intact Peptide | ime | Intact Peptide | ime | Intact Peptide | ime | Intact Peptide |
| | 00 | 4 min | 00 | 0 min | 00 | .5 hr | 00 |
| | | hr | 00* | hr | 00* | .5 hr | 4 |
| 1 hr | 9 | 9 hr | 5 | 0 hr | 1 | 0 hr | 0 |

Some peptide decomposed but was not included in the calculation of the areas of the peaks

Example 32

In-Vivo Biodistribution of IMP 221 in BALB/c Mice

Kits were reconstituted with 400 µCi In-111 in 0.5 mL water. The In-111 kit solution was incubated at room temperature for 10 min and then diluted with 1.5 mL of the cold indium containing pH 7.2, 0.5 M acetate buffer. The labeled peptide was analyzed by ITLC in saturated NaCl. The loose In-111 was at the top 20% of the ITLC strip.

Each mouse was injected with 100 µL (20 µCi) of the In-111 labeled peptide. The animals were anesthetized and sacrificed at 30 minutes, 1 hours, 2 hours, 4 hours, and 24 hours using three mice per time point: Blood, muscle, liver, lungs, kidneys, spleen, large intestine, small intestine, stomach, urine, and tail were collected and counted. The results of the biodistribution study are shown in the following table.

TABLE 9

Biodistribution in BALB/c mice % ID/g of IMP 224 (Dox = N—NH—$C_6H_4$—CO-Lys(DTPA)-Tyr-Lys(DTPA)-$NH_2$ $MH^+$ 1847 radiolabeled with In-111 and saturated with cold In

| Tissue | 30 min | 1 hr | 2 hr | 4 hr | 24 hr |
| --- | --- | --- | --- | --- | --- |
| Liver | 0.57 ± 0.04 | 0.31 ± 0.03 | 0.17 ± 0.03 | 0.17 ± 0.01 | 0.13 ± 0.02 |
| Spleen | 0.57 ± 0.18 | 0.27 ± 0.06 | 0.12 ± 0.01 | 0.11 ± 0.01 | 0.07 ± 0.00 |
| Kidney | 8.45 ± 1.79 | 5.36 ± 1.01 | 3.75 ± 0.52 | 4.03 ± 0.45 | 2.12 ± 0.17 |
| Lungs | 1.61 ± 0.34 | 0.99 ± 0.26 | 0.25 ± 0.02 | 0.17 ± 0.02 | 0.09 ± 0.02 |
| Blood | 1.44 ± 0.28 | 0.54 ± 0.12 | 0.12 ± 0.01 | 0.10 ± 0.01 | 0.02 ± 0.00 |
| Stomach | 0.61 ± 0.07 | 0.15 ± 0.07 | 0.05 ± 0.01 | 0.06 ± 0.02 | 0.04 ± 0.02 |
| Small Int. | 0.72 ± 0.08 | 0.37 ± 0.19 | 0.09 ± 0.01 | 0.09 ± 0.03 | 0.05 ± 0.01 |
| Large Int. | 0.59 ± 0.43 | 0.18 ± 0.04 | 0.38 ± 0.15 | 0.30 ± 0.06 | 0.08 ± 0.03 |
| Muscle | 0.51 ± 0.19 | 0.21 ± 0.08 | 0.03 ± 0.02 | 0.02 ± 0.00 | 0.01 ± 0.00 |
| Urine | 1553 | 1400 ± 421 | 19.1 | 1.72 ± 0.67 | 0.42 ± 0.18 |
| Tail | 3.66 ± 0.43 | 1.90 ± 0.09 | 0.46 ± 0.09 | 0.24 ± 0.03 | 0.58 ± 0.22 |

Example 33

In-Vivo Stability and Clearance of IMP 224

Kits were reconstituted with 4 mCi In-111 in 0.5 mL water. The In-11 kit was incubated at room temperature for 10 min and then diluted with 0.5 mL of the cold indium containing 0.5 M pH 7.2 acetate buffer. The labeled peptide was analyzed by ITLC in saturated NaCl. The loose In-111 was at the top 20% of the ITLC strip.

Each mouse was injected with 100 µL (400 µCi) of the In-111 labeled peptide. The animals were anesthetized and sacrificed at 30 min and 1 hr using two animals per time point. The serum and urine samples were collected, stored on ice, and sent on ice as soon as possible for HPLC analysis. The HPLC (by size exclusion chromatography) of the urine samples showed that the In-111 labeled peptide could still bind to the antibody. The reverse phase HPLC analysis showed that the radiolabeled peptide was excreted intact in the urine. The amount of activity remaining in the serum was too low to be analyzed by reverse phase HPLC due to the poor sensitivity of the detector. by reverse phase HPLC and the labeled peptide was shown to be intact. Doxorubicin has 95% hepatobiliary clearance. Thus, by attaching the bis DTPA peptide in a hydrolyzeable manner, the biodistribution of the drug is altered to give ~100% renal excretion. This renders the drug far less toxic because all of the nontargeted drug is rapidly excreted intact.

TABLE 10

Activity Recovered in The Urine and Serum

| | 30 min | | 1 hr | |
| --- | --- | --- | --- | --- |
| Tissue | Animal #1 | Animal #2 | Animal #1 | Animal #2 |
| Urine | 220 µCi | 133 µCi | 41.1 µCi | 273 µCi |
| Serum | 1.92 µCi | 3.64 µCi | 1.21 µCi | 1.27 µCi |

Example 34

Pretargeting Experiments with IMP 224 and IMP 225

A lyophilized kit of IMP 224 containing 10 micrograms of peptide was used. The kit was lyophilized in 2 mL vials and reconstituted with 1 mL sterile water. A 0.5 mL aliquot was removed and mixed with 1.0 mCi In-111. The In-111 kit solution was incubated at room termperature for 10 minutes then 0.1 mL was removed and diluted with 1.9 mL of the cold indium containing acetate buffer BM 8–12 in a sterile vial. The labeled peptide was analyzed by ITLC in saturated NaCl. The loose In-111 was at the top 20% of the ITLC strip.

Female nude mice (Taconic NCRNU, 3–4 weeks old) with GW 39 tumor xenografts were used for the pretargeting experiments. Tumors were 0.3–0.8 g. Each animal was injected with 100 microliters (5 µCi, 15 µg, 1.5×10$^{-10}$ mol) of the I-125 labeled antibody F6×734-F(ab')$_2$.

Seventy two hours later, each mouse was injected with 100 µL (10 µCi) of the In-111 labeled peptide. The animals were anesthetized and sacrificed at 1 hour, 4 hours and 24 hours using five mice per time point. Tumor, blood, muscle, liver, lungs, kidneys, spleen, large intestine, small intestine, stomach, urine and tail were collected and counted.

The experiment was repeated with a lyophilized kit of IMP 225 (Ac-Cys(Dox-COCH$_2$-)-Lys(DTPA)-Tyr-Lys (DTPA)-NH$_2$ (SEQ ID NO: 5) MNa$^+$1938), containing 11 micrograms of peptide.

TABLE 11

Biodistribution of In-111-IMP-224 in nude mice bearing GW-39 tumor xenografts, previously given F6 x 734-F(ab')$_2$ 72 h earlier. Data in % ID/g tissue. n = 5.

| Tissue | 1 h | | 4 h | | 24 h | |
|---|---|---|---|---|---|---|
| | I-125 | In-111 | I-125 | n-111 | I-125 | n-111 |
| GW-39 | 10.0 ± 1.5 | 10.3 ± 1.7 | 9.8 ± 2.6 | 11.0 ± 2.0 | 8.8 ± 1.2 | 9.7 ± 1.1 |
| Liver | 0.1 ± 0.0 | 0.4 ± 0.1 | 0.1 ± 0.0 | 0.3 ± 0.0 | 0.1 ± 0.0 | 0.3 ± 0.0 |
| Spleen | 0.1 ± 0.0 | 0.4 ± 0.1 | 0.1 ± 0.0 | 0.2 ± 0.0 | 0.1 ± 0.0 | 0.2 ± 0.0 |
| Kidney | 0.3 ± 0.1 | 3.5 ± 0.6 | 0.2 ± 0.0 | 2.8 ± 0.3 | 0.2 ± 0.0 | 1.9 ± 0.2 |
| Lungs | 0.2 ± 0.0 | 0.8 ± 0.2 | 0.2 ± 0.0 | 0.4 ± 0.0 | 0.2 ± 0.0 | 0.1 ± 0.0 |
| Blood | 0.4 ± 0.1 | 1.8 ± 0.6 | 0.4 ± 0.1 | 0.9 ± 0.2 | 0.4 ± 0.0 | 0.2 ± 0.0 |
| Stomach | 0.5 ± 0.2 | 0.8 ± 1.3 | 0.5 ± 0.2 | 0.1 ± 0.0 | 0.7 ± 0.2 | 0.1 ± 0.0 |
| Small Int. | 0.1 ± 0.0 | 0.5 ± 0.4 | 0.1 ± 0.0 | 0.2 ± 0.0 | 0.1 ± 0.0 | 0.1 ± 0.0 |
| Large Int. | 0.1 ± 0.0 | 0.1 ± 0.0 | 0.1 ± 0.0 | 0.3 ± 0.1 | 0.1 ± 0.1 | 0.1 ± 0.1 |
| Muscle | 0.0 ± 0.0 | 0.3 ± 0.2 | 0.0 ± 0.0 | 0.0 ± 0.0 | 0.0 ± 0.0 | 0.0 ± 0.0 |
| Urine | 1.1 ± 2.0 | 168 ± 106 | 1.8 ± 0.6 | 31.8 ± 31 | 0.9 ± 0.2 | 1.2 ± 0.2 |
| Tail | 0.1 ± 0.0 | 1.1 ± 0.2 | 0.1 ± 0.0 | 0.4 ± 0.1 | 0.2 ± 0.0 | 0.2 ± 0.0 |

TABLE 12

Biodistribution of In-111-IMP-224 in nude mice bearing GW-39 tumor xenografts, previously given F6 x 734-F(ab')$_2$ 72 h earlier. Data in tumor-to-normal organ ratios. n = 5.

| Tissue | 1 h | | 4 h | | 24 h | |
|---|---|---|---|---|---|---|
| | I-125 | In-111 | I-125 | n-111 | I-125 | n-111 |
| GW-39 | 1 | 1 | 1 | 1 | 1 | 1 |
| Liver | 85.4 ± 25 | 24.0 ± 5.9 | 81.8 ± 25 | 35.4 ± 6.9 | 61.1 ± 8.5 | 31.6 ± 5.8 |
| Spleen | 81.0 ± 34 | 28.7 ± 8.7 | 74.5 ± 25 | 44.7 ± 10 | 60.8 ± 8.6 | 47.0 ± 2.2 |
| Kidney | 39.7 ± 9.4 | 3.0 ± 0.5 | 57.1 ± 14 | 3.9 ± 0.5 | 39.6 ± 4.8 | 5.0 ± 0.5 |
| Lungs | 51.2 ± 10 | 13.4 ± 2.7 | 50.7 ± 10 | 30.1 ± 4.9 | 50.3 ± 10 | 69.0 ± 9.4 |
| Blood | 25.2 ± 8.3 | 6.1 ± 2.5 | 22.9 ± 7 | 12.8 ± 2.0 | 21.8 ± 4.2 | 41.8 ± 6.3 |
| Stomach | 21.0 ± 6.7 | 48.7 ± 37 | 22.1 ± 7 | 128 ± 46 | 14.9 ± 6.0 | 147 ± 39 |
| Small Int. | 137 ± 41 | 31.9 ± 18 | 128 ± 37 | 51.6 ± 14 | 102 ± 3.7 | 110 ± 13 |
| Large Int. | 136 ± 32 | 87.1 ± 35 | 130 ± 39 | 45.6 ± 19 | 113 ± 12 | 92.4 ± 38 |
| Muscle | 209 ± 86 | 38.6 ± 13 | 1396 ± | 727 ± 797 | 233 ± 42 | 283 ± 46 |
| Urine | 11.0 ± 23 | 0.3 ± 0.5 | 6.3 ± 4.2 | 0.71 ± 0.6 | 9.8 ± 1.9 | 8.3 ± 1.3 |
| Tail | 72.7 ± 20 | 9.4 ± 2.8 | 73.6 ± 20 | 26.4 ± 5.2 | 53.9 ± 10 | 55.9 ± 5.7 |

TABLE 13

Biodistribution of In-111-IMP-225 in nude mice bearing GW-39 tumor xenografts, previously given F6 x 734-F(ab')$_2$ 72 h earlier. Data in % ID/g tissue. n = 5.

| Tissue | 1 h | | 4 h | | 24 h | |
|---|---|---|---|---|---|---|
| | I-125 | In-111 | I-125 | n-111 | I-125 | n-111 |
| GW-39 | 6.2 ± 5.9 | 14.6 ± 14 | 10.5 ± 3.8 | 16.5 ± 4.8 | 8.3 ± 3.0 | 10.1 ± 2.3 |
| Liver | 0.1 ± 0.1 | 0.4 ± 0.2 | 0.2 ± 0.0 | 0.4 ± 0.1 | 0.1 ± 0.0 | 0.3 ± 0.1 |
| Spleen | 0.5 ± 0.7 | 1.6 ± 2.4 | 0.2 ± 0.1 | 0.4 ± 0.1 | 0.1 ± 0.0 | 0.4 ± 0.1 |
| Kidney | 0.3 ± 0.1 | 3.8 ± 0.9 | 0.3 ± 0.1 | 3.8 ± 0.4 | 0.2 ± 0.1 | 1.7 ± 0.3 |
| Lungs | 0.3 ± 0.1 | 0.8 ± 0.4 | 0.3 ± 0.0 | 0.6 ± 0.1 | 0.2 ± 0.1 | 0.2 ± 0.1 |
| Blood | 0.5 ± 0.1 | 2.0 ± 0.4 | 0.8 ± 0.4 | 1.3 ± 0.2 | 0.3 ± 0.1 | 0.4 ± 0.2 |
| Stomach | 0.1 ± 0.2 | 1.1 ± 0.9 | 0.8 ± 0.4 | 0.4 ± 0.2 | 0.3 ± 0.0 | 0.1 ± 0.0 |

TABLE 13-continued

Biodistribution of In-111-IMP-225 in nude mice bearing GW-39 tumor xenografts, previously given F6 x 734-F(ab')$_2$ 72 h earlier. Data in % ID/g tissue. n = 5.

| Tissue | 1 h | | 4 h 5. | | 24 h 6. | |
|---|---|---|---|---|---|---|
| | I-125 | In-111 | I-125 | n-111 | I-125 | n-111 |
| Small Int. | 0.1 ± 0.0 | 0.4 ± 0.1 | 0.1 ± 0.0 | 0.3 ± 0.2 | 0.1 ± 0.0 | 0.1 ± 0.0 |
| Large Int. | 0.1 ± 0.0 | 0.2 ± 0.0 | 0.1 ± 0.0 | 0.3 ± 0.1 | 0.1 ± 0.0 | 0.1 ± 0.0 |
| Muscle | 0.0 ± 0.0 | 0.3 ± 0.2 | 0.1 ± 0.0 | 0.2 ± 0.0 | 0.0 ± 0.0 | 0.1 ± 0.0 |
| Urine | 2.8 ± 3.4 | 110 ± 40 | 2.0 ± 1.0 | 13.5 ± 6.4 | 0.3 ± 0.3 | 0.7 ± 0.4 |
| Tail | 0.4 ± 0.2 | 1.2 ± 0.1 | 0.2 ± 0.0 | 0.8 ± 0.2 | 0.1 ± 0.1 | 0.5 ± 0.7 |

Combinations of the bi-specific constructs described in the present invention or others of similar specificities are suitable for pretargeted RAIT, where IMP-192 peptide and its analogues are labeled with therapeutic radioisotopes such as 188-Re, 213-Bi, 67-Cu and the like. It will be recognized that therapeutic chelates can be conjugated to peptides that have other than chelate epitopes for recognition by bsAbs, as described above.

It will be appreciated as well that detectable radiolabels can be directed to a site of interest, e.g. a tumor, which is to be excised or otherwise detected and/or treated in intraoperative, endoscopic, intravascular or other similar procedures, using the pretargeting methods of the present invention, in combination with various linkers. The pretargeting is effected with non-radioactive bsAbs and the eventual administration and localization of the low molecular weight radiolabeled linker, and clearance of unbound linker, are both comparatively rapid, compatible with surgical procedures that should avoid needless delay and which can use radioisotopes with short half-lives. Additionally, the disclosed therapies can be used for post-surgical radioimmunotherapy protocols to ensure the eradication of residual tumor cells.

All references cited herein are hereby incorporated herein by reference in their entireties.

Additional references of interest include the following:

Bamias, A., and Epenetos, A. A. Two-step strategies for the diagnosis and treatment of cancer with bioconjugates. *Antibody, Immunoconjugates, Radiopharm.* 1992; 5: 385–395.

Barbet, J., Peltier, P., Bardet, S., Vuillez, J P., Bachelot, I., Denet, S., Olivier, P., Lecia, F., Corcuff, B., Huglo, D., Proye, C., Rouvier, E., Meyer, P., Chatal, J. F. Radioimmunodetection of medullary thyroid carcinoma using indium-1 bivalent hapten and anti-CEAxanti-DTPA-indium bispecifc antibody. *J. Nucl. Med.* 1998; 39:1172–1178.

Bos, E S., Kuijpers, W H A., Meesters-Winters, M., Pham, D T., deHaan, A S., van Doormalen, A m., Kasperson, F. M., vanBoeckel, CAA and Gouegeon-Bertrand, F. In vitro evaluation of DNA—DNA hybridization as a two-step approach in radioimmunotherapy of cancer. *Cancer Res.* 1994; 54:3479–3486.

Gautherot, E., Bouhou, J., LeDoussal, J-M., Manetti, C., Martin, M., Rouvier, E., Barbet, J. Therapy for colon carcinoma xenografts with bi-specific antibody-targeted, iodine-131-labeled bivalent hapten. *Cancer suppl.* 1997; 80: 2618–2623.

Gautherot, E., Bouhou, J., Loucif, E., Manetti, C., Martin, M., LeDoussal, J. M., Rouvier, E., Barbet, J. Radioimmunotherapy of LS174T colon carcinoma in nude mice using an iodine-131-labeled bivalent hapten combined with an anti-CEAxanti-indium-DTPA bi-specific antibody. *J. Nucl. Med.* Suppl. 1997; 38: 7p.

Goodwin, D. A., Meares, C F., McCall, M J., McTigue, M., Chaovapong, W. Pre-targeted immunoscintigraphy of murine tumors with indium-111-labeled bifunctional haptens. *J. Nucl. Med.* 1988; 29:226–234.

Greenwood, F. C. and Hunter, W. M. The preparation of I-131 labeled human growth hormone of high specific radioactivity. *Biochem.* 1963; 89:114–123.

Hawkins, G. A., McCabe, R. P., Kim, C.-H., Subramanian, R., Bredehorst, R., McCullers, G. A., Vogel, C.-W., Hanna, M. G. Jr., and Pomata, N. Delivery of radionuclides to pretargeted monoclonal antibodies using dihydrofolate reductase and methotrexate in an affinity system. *Cancer Res.* 1993; 53: 2368–2373.

Kranenborg, M. h., Boerman, O. C., Oosterwijk-Wakka, j., weijert, M., Corstens, F., Oosterwijk, E. Development and characterization of anti-renal cell carcinomaxantichelate bi-specific monoclonal antibodies for two-phase targeting of renal cell carcinoma. *Cancer Res.* (suppl) 1995; 55: 5864s–5867s Penefsky, H. S. A centrifuged column procedure for the measurement of ligand binding by beef heart F1. Part G. *Methods Enzymol.* 1979; 56:527–530.

Schuhmacher, J., Klivenyi, G., Matys, R., Stadler, M., Regiert, T., Hauser, H., Doll, J., Maier-Borst, W., Zoller, M. Multistep tumor targeting in nude mice using bi-specific antibodies and a gallium chelate suitable for immunocintigraphy with positron emission tomography. *Cancer Res.* 1995; 55, 115–123.

Sharkey, R M., Karacay, Griffiths, G L., Behr, T M., Blumenthal, R D., Mattes, M J., Hansen, H J., Goldenberg. Development of a streptavidin-anti-carcinoembryonic ntigen antibody, radiolabeled biotin pretargeting method for radioimmunotherapy of colorectal cancer. Studies in a human colon cancer xenograft model. *Bioconjugate Chem* 1997; 8:595–604.

Stickney, D R., Anderson, L D., Slater, J B., Ahlem, C N., Kirk, G A., Schweighardt, S A and Frincke, J M. Bifunctional antibody: a binary radiopharmaceutical delivery system for imaging colorectal carcinoma. *Cancer Res.* 1991; 51: 6650–6655.

What is claimed is:

1. A method of preparing a bi-specific Fab-scFv fusion protein having at least one arm that specifically binds a targeted tissue and at least one other arm that specifically binds a targetable conjugate which comprises a carrier portion which comprises or bears at least one epitope recognizable by said at least one other arm of said bi-specific antibody or antibody fragment, and one or more conjugated therapeutic or diagnostic agents, or enzymes, comprising:

(1) (A) introducing into a mammalian host cell a recombinant DNA construct comprising an expression cassette capable of producing in said host cell a fragment of said bi-specific fusion protein, wherein said construct comprises, in the 5' to 3' direction of transcription, a transcriptional initiation regulatory region functional in said mammalian host cell, a translational initiation regulatory region functional in said mammalian host cell, a DNA sequence encoding a scFv linked to a Fd fragment, and a transcriptional and translational ter nation regulatory region functional in said mammalian host cell, wherein expression of said fragment of said bi-specific fusion protein is under the control of said regulatory regions;

(B) co-introducing into said mammalian host cell a recombinant DNA construct comprising an expression cassette capable of producing in said mammalian host cell a light-chain antibody fragment which is complementary to said Fd fragment in (A) and which when associated with said Fd fragment forms a Fab fragment whose binding site is specific for said targeted tissue, wherein said construct comprises, in the 5' to 3' direction of transcription, a transcriptional initiation regulatory region functional in said mammalian host cell, a translational initiation regulatory region functional in said mammalian host cell, a DNA sequence encoding a light-chain antibody fragment, and a transcriptional and translational termination regulatory region functional in said mammalian host cell, wherein expression of said light-chain antibody fragment is under the control of said regulatory regions;

(C) growing said cell; and (D) isolating said bi-specific Fab-scFv fusion protein, or (2) (A) introducing into a first mammalian host cell a recombinant DNA construct comprising an expression cassette capable of producing in said first mammalian host cell a fragment of said bi-specific fusion protein, wherein said construct comprises, in the 5' to 3' direction of transcription, a transcriptional initiation regulatory region functional in said first mammalian host cell, a translational initiation regulatory region functional in said first mammalian host cell, a DNA sequence encoding a scFv linked to a Fd fragment, and a transcriptional and translational termination regulatory region functional in said first mammalian host cell, wherein expression of said fragment of said bi-specific fusion protein is under the control of said regulatory regions;

(B) introducing into a second mammalian host cell a recombinant DNA construct comprising an expression cassette capable of producing in said second mammalian host cell a light-chain antibody fragment which is complementary to said Fd fragment in (2)(A) and which when associated with said Fd fragment forms a Fab fragment whose binding site is specific for said targeted tissue, wherein said construct comprises, in the 5' to 3' direction of transcription, a transcriptional initiation regulatory region functional in said second mammalian host cell, a translational initiation regulatory region functional in said second host cell, a DNA sequence encoding a light-chain antibody fragment, and a transcriptional and translational termination regulatory region functional in said second mammalian host cell, wherein expression of said light-chain antibody fragment is under the control of said regulatory regions;

(C) growing said first and second mammalian host cells;

(D) optionally isolating said bi-specific fusion protein fragment and said light-chain antibody fragment;

(E) combining said fragments to produce a Fab-scFv bi-specific fusion protein; and (F) isolating said bi-specific fusion protein.

2. The method of claim 1, wherein said at least one arm that specifically binds a targeted tissue is a humanized Fab fragment.

3. The method of claim 1, wherein said at least one other arm specifically binds said epitope of said targetable conjugate, and said epitope comprises a peptide.

4. The method of claim 1, wherein said at least one other arm specifically binds said epitope of said targetable conjugate, and said epitope comprises a carbohydrate.

5. The method of claim 1, wherein said at least one other arm specifically binds said epitope of said targetable conjugate, and said epitope comprises a hapten.

6. The method of claim 1, wherein said at least one other arm specifically binds said epitope of said targetable conjugate, and said epitope comprises a chelator or a metal-chelate complex.

7. The method of claim 6, wherein said chelator is a hard base chelator for a hard acid cation.

8. The method of claim 6, wherein said chelator is a soft base chelator for a soft acid cation.

9. The method of claim 7, wherein said chelator is a hard base chelator that comprises carboxylate and amine groups.

10. The method of claim 7, wherein said hard base chelator is DTPA, NOTA, DOTA or TETA.

11. The method of claim 1, wherein said at least one other arm specifically binds a tyrosyl-lysine dipeptide.

12. The method of claim 1, wherein said at least one other arm specifically binds Tyr-Lys(DTPA)-N11$_2$, or Lys(DTPA)-Tyr-Lys(DTPA)-NH$_2$.

13. A method of preparing a bi-specific Fab-scFv fusion protein having at least one arm that specifically binds a targeted tissue and at least one other arm that specifically binds a targetable conjugate which comprises a cater portion which comprises or bears at least one epitope recognizable by said at least one other arm of said bi-specific antibody or antibody fragment, and one or more conjugated therapeutic or diagnostic agents, or enzymes, comprising:

(1) (A) introducing into a mammalian host cell a recombinant DNA construct comprising an expression cassette capable of producing in said mammalian host cell a fragment of said bi-specific fusion protein, wherein said construct comprises, in the 5' to 3' direction of transcription, a transcriptional initiation regulatory region functional in said mammalian host cell, a translational initiation regulatory region functional in said mammalian host cell a DNA sequence encoding a scFv linked to a light-chain antibody fragment, and a transcriptional and translational termination regulatory region functional in said mammalian host, cell, wherein expression of said fragment of said bi-specific fusion protein is under the control of said regulatory regions;

(B) co-introducing into said mammalian host cell a recombinant DNA construct comprising an expression cassette capable of producing in said mammalian host cell a Fd fragment which is complementary to said light-chain antibody fragment in (A) and which when associated with said light-chain antibody fragment forms a Fab fragment whose binding site is specific for said targeted tissue, wherein said construct comprises, in the 5' to 3' direction of transcription, a transcriptional initiation regulatory region functional in said mammalian host cell, a translational initiation regulatory region functional in said host cell, a DNA sequence encoding a Fd fragment, and a transcriptional and translational termination regulatory region functional in said mammalian host cell, wherein said expression of Fd fragment is under the control of said regulatory regions;

(C) growing said cell; and (D) isolating said bi-specific Fab-scFv fusion protein, or (2) (A) introducing into a first mammalian host cell a recombinant DNA construct comprising an expression cassette capable of producing in said first mammalian host cell a fragment of said bi-specific fusion protein, wherein said construct comprises, in the 5' to 3' direction of transcription, a transcriptional initiation regulatory region functional in said first mammalian host cell, a translational initiation regulatory region functional in said first mammalian host cell, a DNA sequence encoding a scFv linked to a light-chain antibody fragment, and a transcriptional and translational termination regulatory region functional in said first mammalian host cell, wherein expression of said fragment of said bi-specific fusion protein is under the control of said regulatory regions;

(B) introducing into a second mammalian host cell a recombinant DNA construct comprising an expression cassette capable of producing in said second mammalian host cell a Fd fragment which is complementary to said light-chain antibody fragment in (2)(A) and which when associated with said light-chain antibody fragment forms a Fab fragment whose binding site is specific for said targeted tissue, wherein said construct comprises, in the 5' to 3' direction of transcription, a transcriptional initiation regulatory region functional in said second mammalian host cell, a translational initiation regulatory region functional in said second mammalian host cell, a DNA sequence encoding a Fd fragment, and a transcriptional and translational termination regulatory region functional in said second mammalian host cell, wherein expression of said Fd fragment is under the control of said regulatory regions;

(C) growing said first and second mammalian host cells;

(D) optionally isolating said bi-specific fusion protein fragment and said Fd fragment; and (E) combining said fragments to produce a bi-specific Fab-scFv fusion protein; and (F) isolating said bi-specific fusion protein.

\* \* \* \* \*